United States Patent
Carlsson et al.

(10) Patent No.: US 10,702,512 B2
(45) Date of Patent: Jul. 7, 2020

(54) TREATMENT OF DEBILITATING FATIGUE

(71) Applicant: A. CARLSSON RESEARCH AB, Göteborg (SE)

(72) Inventors: Arvid Carlsson, Göteborg (SE); Carl-Gerhard Gottfries, Göteborg (SE)

(73) Assignee: A. CARLSSON RESEARCH AB, Göteborg (SE)

( * ) Notice: Subject to any disclaimer, the term of this patent is extended or adjusted under 35 U.S.C. 154(b) by 0 days.

(21) Appl. No.: 15/572,409

(22) PCT Filed: May 11, 2016

(86) PCT No.: PCT/EP2016/060562
§ 371 (c)(1),
(2) Date: Nov. 7, 2017

(87) PCT Pub. No.: WO2016/180879
PCT Pub. Date: Nov. 17, 2016

(65) Prior Publication Data
US 2018/0169081 A1    Jun. 21, 2018
US 2019/0070156 A2    Mar. 7, 2019

(30) Foreign Application Priority Data
May 13, 2015  (SE) ...................... 1550618

(51) Int. Cl.
*A61K 31/445* (2006.01)
*A61K 45/06* (2006.01)
*A61K 31/137* (2006.01)

(52) U.S. Cl.
CPC ............ *A61K 31/445* (2013.01); *A61K 45/06* (2013.01); *A61K 31/137* (2013.01); *A61K 2300/00* (2013.01)

(58) Field of Classification Search
CPC .............. A61K 2300/00; A61K 31/445; A61K 31/137; A61K 45/06
See application file for complete search history.

(56) References Cited

U.S. PATENT DOCUMENTS

| | | | | |
|---|---|---|---|---|
| 5,462,947 A * | 10/1995 | Svensson | ............ | C07D 207/08 514/317 |
| 6,903,120 B2 * | 6/2005 | Sonesson | ............ | C07D 211/18 514/254.1 |
| 2003/0191149 A1 * | 10/2003 | McCall | ................ | A61K 31/445 514/292 |
| 2004/0192766 A1 * | 9/2004 | Sanchez | ............... | A61K 31/343 514/469 |
| 2006/0154938 A1 | 7/2006 | Kikuchi et al. | | |
| 2007/0259952 A1 * | 11/2007 | Svensson | ............ | A61K 31/343 514/469 |
| 2010/0197712 A1 * | 8/2010 | Carlsson | ............ | A61K 31/435 514/277 |
| 2013/0197032 A1 * | 8/2013 | Carlsson | ............ | A61K 31/445 514/317 |

FOREIGN PATENT DOCUMENTS

| | | |
|---|---|---|
| EP | 0641320 B1 | 5/2001 |
| WO | WO 01/46145 | 6/2001 |
| WO | WO 01/81343 | 11/2001 |
| WO | WO 2004/010932 | 2/2004 |
| WO | WO 2008/155357 | 12/2008 |

OTHER PUBLICATIONS

Carlsson et al. (Acta Neuropsychiatrica, 2012, 24(5), p. 266-274). (Year: 2012).*
Natesan (The J of Pharmacology and Experimental Therapeutics, 2006). (Year: 2006).*
Moret, Neuropsychiatric Disease and Treatment, 2005, 301-309 (Year: 2005).*
Kim, https://www.healthline.com/health/depression/connbination-therapies#1, 2016 (Year: 2016).*
Afari et al., "Chronic Fatigue Syndrome: A Review", Am J. Psychiatry, 2003, 160:221-236.
Beck et al., "An Inventory for Measuring Depression", Arch Gen Psychiatry, 1961, 4:561-571.
Carruthers et al., "Myalgic encephalomyelitis: International Consensus Criteria", Journal of Internal Medicine, 2011, 270(4):327-338.
Carruthers et al., "Myalgic Encephalomyelitis/Chronic Fatigue Syndrome: Clinical Working Case Definition, Diagnostic and Treatment Protocols", Journal of Chronic Fatigue Syndrome, 2003, 11(1):7-36.
Chambers et al., "Interventions for the treatment, management and rehabilitation of patients with chronic fatigue syndrome/myalgic encephalomyelitis: an updated systematic review", Journal of the Royal Society of Medicine, 2006, 99:506-520.
Fukuda et al., "The Chronic Fatigue Syndrome: A Comprehensive Approach to Its Definition and Study", Annals of Internal Medicine, 1994, 121(12): 953-959.
Guy, "Clinical Global Impressions (CGI) Scale", Retrieved on Jun. 12, 2009 from http://sakai.ohsu.edu/access/content/user/brodym/N574A%20Spring08/appendix/.
Johansson et al., "A self-assessment questionnaire for mental fatigue and related symptoms after neurological disorders and injuries", Brain Injury, 2010, 24(1): 2-12.
Johansson et al., "Placebo-controlled cross-over study of the monoaminergic stabiliser (−)-OSU6162 in mental fatigue following stroke or traumatic brain injury", Acta Neuropsychiatrica, 2012, p. 1-9.

(Continued)

Primary Examiner — Umamaheswari Ramachandran
(74) Attorney, Agent, or Firm — James S. Keddie; Bozicevic, Field & Francis LLP

(57) ABSTRACT

The present disclosure relates to a dopamine stabilizing agent and an anti-depressive agent for use in the treatment of disorders characterized by debilitating fatigue, such as myalgic encephalomyelitis (ME)/Chronic fatigue syndrome (CFS), fibromyalgia (FM) and depression, as well as of combinations thereof. Related treatment methods, pharmaceutical compositions and combination kits are also disclosed.

13 Claims, 9 Drawing Sheets

(56) References Cited

OTHER PUBLICATIONS

Regland et al., "Homozygous thermolabile methylenetetrahydrofolate reductase in schizophrenia-like psychosis", J Neural Transm, 1997, 104: 931-941.

Regland et al., "Nickel Allergy Is Found in a Majority of Women with Chronic Fatigue Syndrome and Muscle Pain—And May Be Triggered by Cigarette Smoke and Dietary Nickel Intake", Journal of Chronic Fatigue Syndrome, 2001, 8 (1): 57-65.

Rimes et al., "Treatments for chronic fatigue syndrome", Occupational Medicine, 2005, 55:32-39.

Van Houdenhove et al., "Chronic fatigue syndrome: is there a role for non-antidepressant pharmacotherapy?", Expert Opin. PHarmacother., 2010, 11(2):215-223.

Wu et al., "Psychological Associations of Poststroke Fatigue A Systematic Review and Meta-Analysis", Downloaded from http://stroke.ahajournals.org/ at Goteborgs Universitet on Jan. 8, 2015, p. 1778-1783.

Zachrisson et al., "Treatment with *Staphylococcus* toxoid in fibromyalgia/chronic fatigue syndrome—a randomised controlled trial", European Journal of Pain, 2002, 6: 455-466.

Zachrisson et al., "A rating scale for fibromyalgia and chronic fatigue syndrome (the FibroFatigue scale)", Journal of Psychosomatic Research, 2002, 52: 501-509.

Zachrisson et al., "Immune Modulation with a Staphylococcal Preparation in Fibromyalgia/Chronic Fatigue Syndrome: Relation Between Antibody Levels and Clinical Improvement", Eur J Clin Microbiol Infect Dis, 2004, 23:98-105.

Moncrieff, "The creation of the concept of an antidepressant: An historical analysis", Social Science & Medicine, 2008, 66: 2346-2355.

Pae et al., "Pharmacological treatment of chronic fatigue syndrome: focusing on the role of antidepressants", Expert Opinion on Pharmacotherapy, 2009, 10 (10): 1561-1570.

Tahar et al., "Effects of acute and repeated treatment with a novel dopamine D2 receptor ligand on L-DOPA-induced dyskinesias in MPTP monkeys", European Journal of Pharmacology, 2001, 412:247-254.

Nilsson et al., "A randomised controlled trial of the monoaminergic stabiliser (− )-OSU6162 in treatment of myalgic encephalomyelitis/chronic fatigue syndrome", Acta Neuropsychiatrica, 2018, DOI: 10.1017/neu.2017.35, pp. 148-157.

Burstein et al., "II. In vitro evidence that (2)-OSU6162 and (+)-0SU6162 produce their behavioral effects through 5-HT2A serotonin and D2 dopamine receptors", J. Neural Transm, 2011, 118(11):1523-1533. doi: 10.1007/s00702-011-0701-y.

Carlsson et al., "I. In vivo evidence for partial agonist effects of (2)-OSU6162 and (+)-OSU6162 on 5-HT2A serotonin receptors", J. Neural Transm,2011, 118(11):1511-1522. doi: 10.1007/s00702-011-0704-8.

* cited by examiner

|  | Screening | Random | Check 1 | Check2 | Check3 | Check4 |
|---|---|---|---|---|---|---|
|  | Visit 1 | Visit 2 | Visit 3 | Visit 4 | Telephone check-up | Visit 5 |
| On site visit | Day-7 | Day 1 | Day 7 | Day 14 | Day 21 | Day 42 |
| Week (assess. point) | -1 (A) | 0 (B) | 1 (C) | 2 (D) |  | 6 (E) |
| Informed consent | X |  |  |  |  |  |
| Inclusion/exclusion | X | X |  |  |  |  |
| ME history | X |  |  |  |  |  |
| MINI | X |  |  |  |  |  |
| Physical exam | X | X | X | X |  | X |
| Vital signs | X | X | X | X |  | X |
| ECG | X |  |  | X |  |  |
| Blood samples | X |  |  | X |  |  |
| Fukuda and ICC criteria | X |  |  |  |  |  |
| Mental fatigue scale | X | X | X | X |  | X |
| FibroFatigue scale | X | X | X | X |  | X |
| Beck scale | X | X | X | X |  | X |
| VAS pain | X | X | X | X |  | X |
| Psychological tests |  | X |  | X |  |  |
| CGI-C |  |  | X | X |  | X |
| Rebound/Withdrawal |  |  |  |  | X | X |
| Adverse events |  | X | X | X | X | X |
| Drug dispensation |  | X | X |  |  |  |
| Drug compliance |  |  | X | X |  |  |
| Concomitant medication | X | X | X | X |  | X |

| | maximal score | placebo | | (-)-OSU6162 | |
|---|---|---|---|---|---|
| | | no AD | AD | no AD | AD |
| Females / males | - | 15 / 4 | 10 / 1 | 15 / 4 | 10 / 1 |
| Age (years) | - | 44,5 ( 7,8 ) | 52,5 ( 10,4 ) | 46,2 ( 13,6 ) | 46,5 ( 11,0 ) |
| Weight (kg) | - | 79,6 ( 20,1 ) | 74,8 ( 8,2 ) | 73,2 ( 11,5 ) | 77,2 ( 15,2 ) |
| Body mass index (kg/m$^2$) | - | 26,7 ( 5,0 ) | 27,2 ( 2,6 ) | 26,2 ( 5,0 ) | 28,0 ( 5,6 ) |
| Years since diagnosis | - | 8,3 ( 8,3 ) | 12,3 ( 12,3 ) | 9,5 ( 12,3 ) | 3,6 ( 3,1 ) |
| FF total score | | 37,9 ( 6,7 ) | 38,8 ( 6,2 ) | 35,4 ( 7,3 ) | 38,6 ( 7,2 ) |
| MFS total score | 44 | 25,8 ( 3,7 ) | 25,5 ( 4,9 ) | 23,0 ( 5,7 ) | 25,5 ( 3,9 ) |
| BDI total score | 63 | 16,8 ( 8,0 ) | 18,0 ( 6,7 ) | 14,5 ( 7,6 ) | 18,4 ( 10,1 ) |
| VAS pain | 100 | 53,3 ( 22,6 ) | 49,2 ( 20,6 ) | 39,5 ( 25,7 ) | 38,9 ( 23,0 ) |
| BNIS total score | 50 | 45,1 ( 2,7 ) | 43,5 ( 2,4 ) | 45,6 ( 4,0 ) | 44,8 ( 2,4 ) |
| BNIS konv | | 38,3 ( 13,4 ) | 32,7 ( 11,8 ) | 43,5 ( 16,2 ) | 37,8 ( 12,3 ) |
| Coding | | 49,7 ( 9,4 ) | 47,9 ( 10,0 ) | 51,3 ( 11,9 ) | 50,5 ( 14,0 ) |
| TMT-A | | 31,3 ( 10,1 ) | 36,2 ( 9,8 ) | 31,6 ( 11,3 ) | 35,9 ( 10,2 ) |
| TMT-B | | 76,4 ( 33,8 ) | 73,8 ( 21,8 ) | 67,5 ( 17,3 ) | 78,3 ( 27,1 ) |
| Stroop I | | 14,1 ( 3,4 ) | 15,5 ( 5,5 ) | 13,5 ( 2,7 ) | 14,4 ( 3,6 ) |
| Stroop II | | 20,3 ( 7,7 ) | 18,7 ( 4,8 ) | 19,0 ( 5,2 ) | 20,4 ( 7,2 ) |
| Stroop III | | 29,1 ( 11,0 ) | 25,5 ( 5,5 ) | 25,1 ( 7,8 ) | 30,2 ( 9,8 ) |

AD: On treatment with antidepressants for depression
no AD: Not on treatment with antidepressants for depression

TREATMENT OF DEBILITATING FATIGUE

CROSS-REFERENCE TO RELATED APPLICATIONS

This application is a § 371 national phase of International Application No. PCT/EP2016/060562, filed on May 11, 2016, which claims the benefit of Swedish Application No. 1550618-1, filed on May 13, 2015, which applications are incorporated by reference herein.

FIELD OF THE INVENTION

The present disclosure relates to a combination of a dopamine stabilizing agent and an anti-depressive agent for use in the treatment of disorders characterized by debilitating fatigue, such as myalgic encephalomyelitis (ME)/Chronic fatigue syndrome (CFS), fibromyalgia (FM) and depression, as well as of combinations thereof. Related treatment methods, pharmaceutical compositions and combination kits are also disclosed.

BACKGROUND

Myalgic encephalomyelitis (ME), also known as Chronic fatigue syndrome (CFS), refers to a group of debilitating medical conditions characterized by persistent fatigue and other specific symptoms that last for a minimum of six months in adults (and 3 months in children or adolescents). This disease is also referred to as systemic exertion intolerance disease (SEID), post-viral fatigue syndrome (PVFS) and chronic fatigue immune dysfunction syndrome (CFIDS).

ME/CFS is characterized by persistent and debilitating fatigue, diffuse musculoskeletal pain, sleep disturbances, neuropsychiatric symptoms and cognitive impairment which cannot be explained by an underlying medical condition. The symptoms of ME/CFS are not caused by ongoing exertion and are not relieved by rest.

ME/CFS is a symptom-based diagnosis or clinical diagnosis without distinguishing physical examination or routine laboratory findings. Infectious, immunological, neuroendocrine, sleep and psychiatric mechanisms have been investigated; however, a unifying etiology for ME/CFS has not yet emerged. The majority of ME/CFS cases start suddenly and they are usually accompanied by a "flu-like illness", while a significant proportion of cases begin within several months of severe adverse stress (Afari N et al (2003), Am J Psychiatr 160 (2): 221-36). Often, there are courses of remission and relapse of symptoms which make the illness difficult to manage. Persons who feel better for a period may overextend their activities, and the result can be a worsening of their symptoms with a relapse of the illness.

ME/CFS often occurs together with other diseases such as fibromyalgia (FM), multiple chemical sensitivities, irritable bowel syndrome and temporomandibular joint disorder. In particular, co-morbidity with fibromyalgia has been studied (Afari N et al, supra). Fibromyalgia is a nonarticular rheumatic syndrome characterized by myalgia and multiple points of focal muscle tenderness to palpation (trigger points). Patients with FM often experience muscle pain aggravated by inactivity or exposure to cold. This condition is often associated with general symptoms, such as sleep disturbances, fatigue, stiffness, headaches and occasionally depression.

Despite the contrasting definitions of the two disorders, 20-70% of patients with fibromyalgia also meet the criteria for chronic fatigue syndrome, and conversely, 35-70 of those with chronic fatigue syndrome-like illnesses have concurrent fibromyalgia (Afari N et al, supra).

ME/CFS is a common disorder. Estimates of the prevalence of ME/CFS range from 0.07% to 2.8% in the general adult population and is lower in children and adolescents (Afari N et al, supra). The prevalence of the related fibromyalgia (FM) is 2-4%. This means that in Sweden at least 40 000 patients suffer from ME/CFS and 270 000 from FM (for review see Zachrisson O (2002); Fatigue Syndrome-aspects on biology, treatment and symptom evaluation [dissertation]. ISBN 91-628-5386-4. Gothenburg University).

Many patients suffering from ME/CFS experience significant functional impairment. Nearly all patients with ME/CFS notice a decrease in social relationships in addition to other unwanted consequences of illness; about one-third are unable to work or study, and another one-third can only work part-time (Afari N et al, supra). Many patients suffering from ME/CFS also experience depression symptoms and are diagnosed with clinical depression, and likewise, patients who suffer from depression often experience symptoms of debilitating fatigue.

Currently, patients suffering from ME/CFS are treated by cognitive behavioral therapy (CBT) or graded exercise therapy (GET), which have shown moderate effectiveness in multiple randomized controlled trials, however many patients do not make recovery (Rimes K A et al (2005), Occupational Medicine 55(1): 32-39; Chambers D et al (2006). Journal of the Royal Society of Medicine 99(10): 506-20). At present, medication plays a minor role in disease management (Van Houdenhove B et al (2010) Expert opinion on pharmacotherapy 11(2): 215-23).

Additionally, many disorders, in addition to ME/CFS and FM, are characterized by symptoms of debilitating fatigue. Such disorders include mental fatigue, post stroke fatigue, Huntington's disease, Parkinson's disease, multiple sclerosis, narcolepsy, post cancer fatigue, fatigue associated with cancer with or without cytostatic treatment, depression and combinations thereof.

Thus there is a large need for novel therapies and treatments to alleviate fatigue symptoms, such as ME/CFS associated fatigue symptoms and fatigue symptoms associated with other clinical indications, and thus the provision thereof remains a matter of substantial interest within the field.

SUMMARY OF THE INVENTION

It is an object of the present disclosure to provide to a new and efficient treatment for patients who are suffering from disorders characterized by persistent and debilitating fatigue.

It is an object of the present disclosure to provide a medicament for use in the treatment of said patients.

It is another object of the present disclosure to provide a method of treatment of a disorder characterized by debilitating fatigue for patients in need thereof.

These and other objects which are evident to the skilled person from the present disclosure are met by different aspects of the invention as claimed in the appended claims and as generally disclosed herein.

The present inventors have unexpectedly found that the clinical outcome of treatment of disorders characterized by debilitating fatigue is significantly improved by the combination of a dopamine stabilizing agent and an anti-depressive agent.

Thus, in the first aspect of the disclosure, there is provided a dopamine stabilizing agent and an anti-depressive agent for use in the treatment of a disorder characterized by debilitating fatigue, wherein said dopamine stabilizing agent is selected from the group consisting of i) a compound of formula I

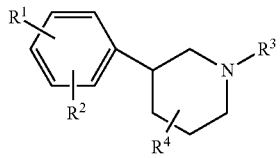

(I)

wherein:

$R^1$ and $R^2$ are independently selected from the group consisting of H, provided that not more than one of $R^1$ and $R^2$ is H, $CONH_2$, OH, CN, $CH_2CN$, $OSO_2CH_3$, $OSO_2CF_3$, $SSO_2CF_3$, COR, $SO_xCH_3$, $SO_xCF_3$, $O(CH_2)_xCF_3$, where x is 0-2, $OSO_2N(R)_2$, $CH=NOR$, COCOOR, $COCOON(R)_2$, $C_{3-8}$ cycloalkyl, $NRSO_2CF_3$, phenyl at position 2, 3 or 4, thienyl, furyl, pyrrolyl, oxazolyl, thiazolyl, N-pyrrolinyl, triazolyl and tetrazolyl of pyridinyl;

$R^3$ is independently selected from the group consisting of H, $CF_3$, $CH_2CF_3$, $C_1$-$C_8$ alkyl, $C_3$-$C_8$ cycloalkyl, $C_4$-$C_9$ cycloalkyl-methyl, $C_2$-$C_8$ alkenyl, $C_2$-$C_8$ alkynyl, 3,3,3-trifluoropropyl, 4,4,4-trifluorobutyl and $CH_2SCH_3$;

$R^4$ and R are independently selected from the group consisting of H, $CF_3CH_2CF_3$, $C_1$-$C_8$ alkyl, $C_3$-$C_8$ cycloalkyl, $C_4$-$C_9$ cycloalkyl-methyl, $C_2$-$C_8$ alkenyl, $C_2$-$C_8$ alkynyl, 3,3,3-trifluoropropyl, 4,4,4-trifluorobutyl and —$(CH_2)m$-$R^5$ where m is 1-8;

$R^5$ is independently selected from the group consisting of phenyl, phenyl substituted with CN, $CF_3$, $CH_2CF_3$, $C_1$-$C_8$ alkyl, $C_3$-$C_8$ cycloalkyl, $C_4$-$C_9$ cycloalkyl-methyl, $C_2$-$C_8$ alkenyl or $C_2$-$C_8$ alkynyl substituent, 2-thiophenyl, 3-thiophenyl, —$NR^6CONR^6R^7$ and —$CONR^6R^7$; and $R^6$ and $R^7$ are independently selected from the group consisting of H, $C_1$-$C_8$ alkyl, $C_3$-$C_8$ cycloalkyl, $C_4$-$C_9$ cycloalkyl-methyl, $C_2$-$C_8$ alkenyl and $C_2$-$C_8$ alkynyl;

ii) a compound of formula II

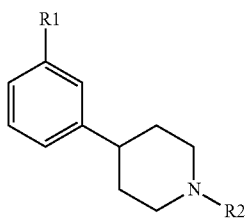

(II)

wherein:

$R_1$ is independently selected from the group consisting of $OSO_2CF_3$, $OSO_2CH_3$, $SOR_3$, $SO_2R^3$, $COCH_3$ and $COCH_2CH_3$, wherein $R_3$ is as defined below; $R_2$ is independently selected from the group consisting of $C_2$-$C_4$ branched or unbranched alkyls, terminal allyl, $CH_2CH_2OCH_3$, $CH_2CH_2CH_2F$, $CH_2CF_3$, 3,3,3-trifluoropropyl and 4,4,4-trifluorobutyl, $R_3$ is independently selected from the group consisting of $C_1$-$C_3$ alkyls, $CF_3$, and $N(CH_3)_2$; and iii) a compound of formula III

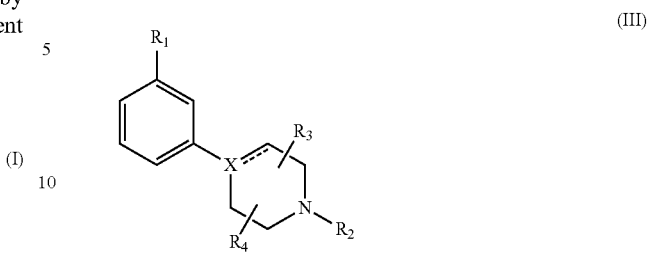

(III)

wherein:

X is independently selected from the group consisting of N, CH and C, provided that X may only be C when the compound comprises a double bond at the dotted line;

$R_1$ is independently selected from the group consisting of $OSO_2CF_3$, $OSO_2CH_3$, $SOR_5$, $SO_2R_5$, $COR_5$, CN, $NO_2$, $CONHR_5$, $CF_3$, 3-thiophene, 2-thiophene, 3-furane, 2-furane, F, Cl, Br, and I, wherein $R_5$ is as defined below;

$R_2$ is independently selected from the group consisting of $C_1$-$C_4$ alkyls, allyls, $CH_2SCH_3$, $CH_2CH_2OCH_3$, $CH_2CH_2CH_2F$, $CH_2CF_3$, 3,3,3-trifluoropropyl, 4,4,4-trifluorobutyl and —$(CH_2)$—$R_6$, wherein $R_6$ is as defined below;

$R_3$ and $R_4$ are independently selected from the group consisting of H and $C_1$-$C_4$ alkyls, provided that both $R_3$ and $R_4$ cannot be H at the same time;

$R_5$ is independently selected from the group consisting of $C_1$-$C_3$ alkyls, $CF_3$ and $N(R_2)_2$, wherein $R_2$ is as defined above; and $R_6$ is independently selected from the group consisting of $C_3$-$C_6$ cycloalkyls, 2-tetrahydrofurane and 3-tetra-hydrofurane;

and pharmaceutically acceptable salts of any one of the compounds of formula I, II or III.

Thus, said dopamine stabilizing agent may be any one of the compounds with formula I, II or III as defined above or a pharmaceutically acceptable salt of any one of the compounds with formula I, II or III.

In one embodiment of the present disclosure, said dopamine stabilizing agent is selected from the group consisting of compounds with formula I or formula II; the group consisting of compounds with formula II or formula III; or the group consisting of compounds with formula I or formula III. In another embodiment, said dopamine stabilizing agent is selected from the group consisting of compounds with formula I. In one embodiment, said dopamine stabilizing agent is selected from the group consisting of compounds with formula II. In one embodiment, said dopamine stabilizing agent is selected from the group consisting of compounds with formula Ill.

Dopamine stabilizing substances of formula I and pharmaceutically acceptable salts thereof have been described in U.S. Pat. No. 5,462,947. U.S. Pat. No. 5,462,947 discloses the compounds belonging to this group and also gives the definitions for the different terms used—see in particular column 4, line 54—column 6, line 25. U.S. Pat. No. 5,462,947 also discloses how these compounds may be obtained—see in particular column 7, lines 26-28 and the Examples.

According to one embodiment, said dopamine stabilizing agent of formula I for use in the treatment as described herein is in the form of a pure enantiomer or a pharmaceutically acceptable salt thereof, such as a pure S-enantiomer or a pharmaceutically acceptable salt thereof.

According to one embodiment, there is provided a dopamine stabilizing agent of formula I for use in the treatment as described herein, wherein $R^1$ is CN, $OSO_2CF_3$, or $SO_2CH_3$ or a pharmaceutically acceptable salt thereof. In one embodiment, $R^1$ is CN. In one embodiment, $R^1$ is $SO_2CH_3$. It may then be preferable that $R^2$ is H and $R^3$ is $C_{1-8}$ alkyl, and further that $R^3$ is n-propyl, and moreover that $R^4$ is H. In one embodiment, $R^1$ is independently selected from the group consisting of CN, $OSO_2CF_3$ and $SO_2CH_3$; $R^2$ is H; $R^3$ is $C_{1-8}$ alkyl, such as n-propyl; and $R^4$ is H.

According to one embodiment, there is provided a dopamine stabilizing agent of formula I for use in the treatment as described herein wherein $R^1$ is 3-OH, $R^2$ is H, $R^3$ is n-propyl and $R^4$ is $C_{2-8}$ alkyl or a pharmaceutically acceptable salt thereof.

According to one embodiment, said dopamine stabilizing agent of formula I for use in the treatment as described herein is (3S)-3-[3-(methylsulfonyl)phenyl]-1-propylpiperidine.

Dopamine stabilizing substances of formula II and pharmaceutically acceptable salts thereof, have been described in U.S. Pat. No. 6,903,120.

According to one embodiment of the present aspect, there is provided a dopamine stabilizing agent of formula II for use in the treatment as described herein wherein $R_1$ is selected from the group consisting of $OSO_2CF_3$, $OSO_2CH_3$, $SO_2CH_3$, $SO_2CF_3$, $COCH_3$, and $SO_2N(CH_3)_2$ or a pharmaceutically acceptable salt thereof. It may then be preferable that $R_1$ is selected from the group consisting of $SO_2CF_3$, $SO_2CH_3$, and $COCH_3$.

According to one embodiment, there is provided a dopamine stabilizing agent of formula II for use in the treatment as described herein wherein $R_2$ is selected from the group consisting of n-propyl and ethyl or a pharmaceutically acceptable salt thereof.

According to one embodiment the compound of formula II is 4-(3-methanesulfonylphenyl)-1-propyl-piperidine.

Dopamine stabilizing substances of formula III and pharmaceutically acceptable salts thereof, have been described in WO 01/46145.

According to one embodiment of the first aspect, there is provided a dopamine stabilizing agent of formula III for use in the treatment as described herein, wherein X is CH or C or a pharmaceutically acceptable salt thereof. It may be preferable that X is CH.

According to one embodiment, there is provided a dopamine stabilizing agent of formula III for use in the treatment as described herein wherein $R_1$ is selected from the group consisting of $OSO_2CF_3$, $OSO_2CH_3$, $SO_2CH_3$, $SO_2CF_3$, $COCH_3$, $CF_3$, CN, $CON(CH_3)_2$, and $SO_2N(CH_3)_2$ or a pharmaceutically acceptable salt thereof. When X is CH it may be preferable that $R_1$ is selected from the group consisting of $SO_2CF_3$, $SO_2CH_3$, $COCH_3$, $CF_3$, and CN.

According to one embodiment, there is provided a dopamine stabilizing agent of formula III for use in the treatment as described herein wherein $R_2$ is selected from the group consisting of n-propyl and ethyl or a pharmaceutically acceptable salt thereof. According to one embodiment, there is provided a dopamine stabilizing agent of formula III for use in the treatment as described herein, wherein X is CH, $R_1$ is $SO_2CH_3$, and $R_2$ is n-propyl or a pharmaceutically acceptable salt thereof.

According to one embodiment the compound of formula III is 4-(3-methanesulfonyl-phenyl)-1-propyl-piperidine.

As stated above, the dopamine stabilizing agent may be a pharmaceutically acceptable salt of a compound of formula I, II or III. The term "pharmaceutically acceptable salt(s)", as used herein, means those salts of compounds of the disclosure that are safe and effective for oral, subcutaneously, intramuscularly or intravenously administration in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide and hydroiodide.

Thus, in one embodiment, there is provided a dopamine stabilizing agent of formula I, II or II for use in the treatment as described herein, wherein said pharmaceutically acceptable salt is hydrochloride, hydrobromide or hydroiodide, such as hydrochloride. In one embodiment, said pharmaceutically acceptable salt is a hydrochloride of a compound of formula I, II or II, such as of a compound of formula I. In one embodiment, said pharmaceutically acceptable salt is (3S)-3-[3-(methylsulfonyl)phenyl]-1-propylpiperidine hydrochloride. In one embodiment, said pharmaceutically acceptable salt is 4-(3-methanesulfonylphenyl)-1-propyl-piperidine hydrochloride. In one embodiment, said pharmaceutically acceptable salt is 4-(3-methanesulfonyl-phenyl)-1-propyl-piperidine hydrochloride.

As used herein, the terms "antidepressants" and "antidepressive agents" refer to medicaments used for the treatment of a major depressive disorder, which is a mental disorder characterized by a pervasive and persistent low mood that is accompanied by low self-esteem and by a loss of interest or pleasure in normally enjoyable activities; and other similar medical conditions. A non-limiting list of major types on anti-depressive agents includes selective serotonin reuptake inhibitors (SSRIs), serotonin-norepinephrine reuptake inhibitors (SNRIs), serotonin modulators and stimulators (SMSs), serotonin reuptake inhibitors (SARIs), norepinephrine reuptake inhibitors (NRIs), tricyclic antidepressants (TCAs), monoamine oxidase inhibitors (MAOIs), tetracyclic antidepressants (TeCAs), noradrenergic and specific serotonergic antidepressant (NaSSAs), buprenorphine, low-dose antipsychotics and St John's wort.

One major class of anti-depressive agents are selective serotonin reuptake inhibitors (SSRIs) which increase the extracellular level of the neurotransmitter serotonin by inhibiting its reuptake into the presynaptic cell and thus increase the level of serotonin in the synaptic cleft available to bind to the postsynaptic receptor. Non-limiting examples of SSRI include citalopram, fluvoxamine, escitalopram, paroxetine, sertaline and flouxetine. Another large class of anti-depressive agents are serotonin-norepinephrine reuptake inhibitors (SNRIs) which are potent inhibitors of the reuptake of serotonin and norepinephrine. Non-limiting examples of SNRIs include venlafaxine, milnacipran, duloxetine, levomilnacipran, desvenlafaxine and sibutramine. The term serotonin modulators and stimulators (SMSs) refers to drugs with a multimodal action specific to the serotonin neurotransmitter system by simultaneously modulating one or more serotonin receptors and inhibiting the reuptake of serotonin. Non-limiting examples of SMSs include vortioxetine and vilazodone. Serotonin reuptake inhibitors (SARIs) are drugs that act by antagonizing serotonin receptors, such as 5-$HT_{2A}$, and inhibiting the reuptake of serotonin, norepinephrine and/or dopamine. The majority of the currently marketed SARIs belong to the phenylpiperazine class of compounds and non-limiting examples of SARIs include etoperidone, lorpiprazole, lubazodone, mepiprazole, nefazodone and trazodone. Also known are tricyclic anti-depressant (TCAs), which are chemical compounds used primarily as antidepressants. Examples of TCA that act to preferentially inhibit the reuptake of serotonin are clomipramine and imipramine and examples of TCA that act to preferentially inhibit the reuptake of norepinephrine include desipramine, dibenzepin, lofepramine, nortriptyline and protriptyline. TCA which are considered to be fairly balanced serotonin-norepinephrine reuptake inhibitors include amitriptyline, amitriptylinoxide, amoxapine, butriptyline, demexiptiline, dimetacrine, dosulepin, doxepin, imipraminoxide, melitracen, metapramine, nitroxazepine, noxiptiline, pipofezine, propizepine and quinupramine. TCAs that act via other mechanisms beside serotonin-norepinephrine reuptake inhibition include but are not limited to amineptine, iprindole, opipramol, tianeptine and trimipramine. Monoamine oxidase inhibitors (MAOIs) are chemicals which inhibit the activity of the monoamine oxidase enzyme family and are also used for the treatment of depression, typically for the treatment of atypical depression where treatment with other anti-depressant has failed. Non-limiting examples of MOAIs include nonselective MAO-A/MAO-B Inhibitors, such as hydrazines (for example isocarboxazid, nialamide, phenelzine and hydracarbazine) and non-hydrazines (for example tranylcypromine); selective MAO-A inhibitors, such as moclobemide, pirlindole and toloxatone; and selective MAO-B Inhibitors, such as rasagiline and selegiline. Additionally, other drugs with monoamine oxidase inhibiting activity may be used for the treatment of depression, such as linezolid which is an antibiotic drug with weak monoamine oxidase inhibiting activity. Also known are tetracyclic antidepressants (TeCAs) and a non-limiting list of TeCAs includes amoxapine, loxapine, maprotiline, mazindol, and setiptiline. Noradrenergic and specific serotonergic antidepressants (NaSSAs) act to block $\alpha_2$-adrenergic autoreceptors and heteroreceptors and enhance adrenergic and serotonergic neurotransmission involved in mood regulation, such as $5\text{-HT}_{1A}$-mediated transmission. Non-limiting examples of NaSSAs include aptazapine, esmirtazapine, setiptiline and S32212. Notably, many of these compounds are also classified as tetracyclic antidepressants (TeCAs) based on their chemical structures. Additionally, other agents, which may act as anti-depressive agents may be useful for the purposes of the present disclosure. Examples of potentially useful additional agents include, but are not limited to, buprenorphine (a semi synthetic opioid derivative of thebaine), low dose anti-phychotic drugs and St John's wort (*Hypericum perforatum*), which is a medicinal herb with antidepressant activity.

The skilled person will appreciate that the above lists of anti-depressive agents are by no means limiting and other agents may be equally useful for the purposes of the present disclosure. Additionally, the skilled person will appreciate that combinations of said anti-depressive agents may used.

Thus, in one embodiment, there is provided a dopamine stabilizing agent and an anti-depressive agent for use in the treatment of a disorder characterized by debilitating fatigue as described herein, wherein said anti-depressive agent is selected from the group consisting of selective serotonin reuptake inhibitors (SSRIs), serotonin-norepinephrine reuptake inhibitors (SNRIs), serotonin modulators and stimulators (SMSs), serotonin reuptake inhibitors (SARIs), norephinephrine reuptake inhibitors (NRIs), tricyclic anti-depressants (TCAs), monoamine oxidase inhibitors (MAOIs), tetracyclic antidepressants (TeCAs), noradrenergic and specific serotonergic antidepressant (NaSSAs), buprenorphine, low-dose antipsychotics and St John's wort, such as a group consisting of selective serotonin reuptake inhibitors (SSRIs), serotonin-norepinephrine reuptake inhibitors (SNRIs), serotonin modulators and stimulators (SMSs), serotonin reuptake inhibitors (SARIs), norephinephrine reuptake inhibitors (NRIs), tricyclic antidepressants (TCAs), tetracyclic antidepressants (TeCAs), noradrenergic and specific serotonergic antidepressant (NaSSAs), buprenorphine, low-dose antipsychotics and St John's wort. In one embodiment, said anti-depressive agent is selected from the group consisting of selective serotonin reuptake inhibitors (SSRI), serotonin-norepinephrine reuptake inhibitors (SNRI) and tricyclic antidepressants (TCAs), such as the group consisting of selective serotonin reuptake inhibitors (SSRI) and serotonin-norepinephrine reuptake inhibitors (SNRI) or combinations thereof. In one embodiment, said selective serotonin reuptake inhibitor (SSRI) or serotonin-norepinephrine reuptake inhibitor (SNRI) is selected from the group consisting of escitalopram, citalopram, sertraline, fluoxetine, paroxetine, duloxetine, amitriptyline, fluvoxamine, dapoxetine, indalpine, zemelidinem venlafaxine, desvenlafaxine, milnacipran, levomilnacipran and sibutramine or combinations thereof, such as the group consisting of escitalopram, citalopram, sertraline, fluoxetine, paroxetine, amitriptyline, fluvoxamine, dapoxetine, indalpine, zemelidinem venlafaxine, desvenlafaxine, milnacipran, levomilnacipran and sibutramine or combinations thereof. In another embodiment, said selective serotonin reuptake inhibitors (SSRI), serotonin-norepinephrine reuptake inhibitors (SNRI) or tricyclic antidepressant (TCAs) is selected from the group consisting of escitalopram, citalopram, sertraline, fluoxetine, paroxetine, duloxetine, amitriptyline and venlafaxine or combinations thereof, such as the group consisting of escitalopram, citalopram, sertraline, fluoxetine, paroxetine, amitriptyline and venlafaxine or combinations thereof.

As mentioned above, the present disclosure is based on the unexpected finding that the clinical outcome of treatment of disorders characterized by debilitating fatigue is significantly improved by the combination of a dopamine stabilizing agent and an anti-depressive agent in the patient. The skilled person will appreciate that a patient may have a therapeutically effective concentration in blood of a dopamine stabilizing agent as defined above and of an anti-depressive agent, irrespective of in which order said agents are administered relative to each other. In other words, the skilled person will appreciate that the co-administration of said agents may be simultaneous or concomitant. As used herein, the term "co-administration" refers to the administration of two or more drugs together, such as administration of the dopamine stabilizing agent as defined herein and an anti-depressive agent.

Thus, in one embodiment, there is provided a dopamine stabilizing agent and an anti-depressive agent for use in treatment as described herein, wherein said use involves concomitant or simultaneous co-administration of said agents. Concomitant administration may be co-administration, wherein said dopamine stabilizing agent and said anti-depressive agent are administered within a predefined time period (irrespective of which agent is administered first). For example, the predefined time period may be 72 hours, 48 hours, 24 hours, 12 hours, 6 hours or 1 hour. Thus, in one embodiment there is provided a dopamine stabilizing agent and an anti-depressive agent for use as defined herein, wherein said co-administration is concomitant administration within less than 72 hours, such as within less than 48 hours, such as within less than 24 hours, such as within less than 12 hours, such as within less than 6 hours, such as within less than 1 hour. In another embodiment, said administration is simultaneous. It will be appreciated that the patient may be on ongoing treatment with an anti-depressive agent at the time point of starting said co-administration, such as treatment that has been ongoing for at least 6 months, such as at least 3 months, such as at least 1 month, such as at least 2 weeks.

In one embodiment, there is provided a dopamine stabilizing agent and an anti-depressive agent for use in the treatment as described herein, wherein at least one or both agents is/are administered orally, subcutaneously, intramuscularly or intravenously, such as orally. The skilled person will appreciate that one or both of said agents may be administered by any one of said administration routes. For example, said dopamine stabilizing agent may be administered subcutaneously while said anti-depressive agent may be administered orally. Alternatively, both agents may be administered by the same administration route. It will be appreciated that non-invasive administration may generally be preferable. Thus, in one embodiment, said dopamine stabilizing agent and said at least one anti-depressive agent are administered orally. In one embodiment, said administration is in a dose of approximately 0.1-45 mg, such as approximately 0.1-5 mg, such as approximately 0.1-2 or such as approximately 1-45 mg, such as approximately 1-30 mg, such as approximately 5-30 mg, such as approximately 10-30 mg, such as 15 mg or 30 mg.

In one embodiment, said administration is at a dose of approximately 1-20 mg, such as approximately 5-20 mg, such as approximately 10-20 mg, such as 15 mg and in another embodiment, said dose is approximately 1-30 mg, such as approximately 15-30 mg, such as approximately 20-30 mg, such as 30 mg.

In one embodiment, wherein said dopamine stabilizing agent is administered orally said dose is approximately 1-45 mg, such as approximately 1-30 mg, such as approximately 5-30 mg, such as approximately 10-30 mg, such as 15 mg or 30 mg. When the administration is subcutaneous or intramuscular, it may be suitable that the administered dose corresponds to approximately half of the oral dose. Thus, in one embodiment, wherein said dopamine stabilizing agent is administered subcutaneously or intramuscularly, the dose is approximately 1-30 mg, such as approximately 1-20 mg, such as approximately 15 mg, 10 mg or 8 mg.

In another embodiment, wherein the dopamine stabilizing agent is administered intravenously, the dose of said agent is approximately 0.1-5 mg, such as approximately 0.1-2 mg.

In order to obtain high patient compliance, that is the degree to which a patient correctly follows medical advice, it is generally considered that the treatment regimes may not be complex in order to for a patient to be able to easily follow them. For example, it may be preferable that the administration of a drug is once, twice or three times a day, such as twice or once a day. Thus, in one embodiment, there is provided a dopamine stabilizing agent and an anti-depressive agent for use as described herein, wherein said dopamine stabilizing agent is administered once, twice or three times a day, such as once or twice a day. To clarify, thus the dopamine stabilizing agent may for example be administered orally twice a day in a dose of 30 mg, resulting in a daily dose of 60 mg. For example, it may be preferred that said dopamine stabilizing agent and an anti-depressive agent are concomitantly administered once, twice or three times a day, such as once or twice a day. It will be appreciated, that said dopamine stabilizing agent and said anti-depressive agent may be administered a different number of times a day. For example, said dopamine stabilizing agent may be administered twice a day and said anti-antidepressive agent may be administered once a day.

As disclosed in the Example section, superior patient outcomes were observed in patients whose blood plasma concentration of dopamine stabilizing agent was approximately 0.1-0.7 µM. In particular, superior outcomes were observed in patients whose blood plasma concentration of dopamine stabilizing agent was approximately 0.3-0.7 µM. Thus, in one embodiment there is provided a dopamine stabilizing agent and at least one anti-depressive agent for use as described herein, wherein, upon administration, the therapeutically effective blood plasma concentration of said dopamine stabilizing agent is approximately 0.1-0.7 µM, such as approximately 0.3-0.7 µM.

As disclosed in the Example section of the present disclosure, a dopamine stabilizing agent as defined herein and an anti-depressive agent may be useful in the treatment of a disorder characterized by debilitating fatigue, which disorder often includes symptoms such as persistent and/or recurrent debilitating fatigue, diffuse musculoskeletal pain, sleep disturbances and subjective cognitive impairment. Non-limiting examples of such disorders include myalgic encephalomyelitis (ME), also known as chronic fatigue syndrome (CFS), which refers to a group of debilitating medical conditions characterized by persistent and debilitating fatigue, diffuse musculoskeletal pain, sleep disturbances, neuropsychiatric symptoms and cognitive impairment that last for a minimum of at least six months in adults. ME/CFS often occurs together with other diseases such as fibromyalgia (FM), multiple chemical sensitivities, irritable bowel syndrome and temporomandibular joint disorder. Additionally, a number of other disorders are also characterized by disabling fatigue. A non-limiting list of such diseases includes FM, mental fatigue, post stroke fatigue, Huntington's disease, Parkinson's disease, multiple sclerosis, narcolepsy, post cancer fatigue, ADHD, depression and combinations thereof. Additionally, fatigue may be associated with cancer with or without cytostatic treatment. The skilled person will appreciate that the disorder characterized by disabling fatigue may be a fatigue disorder or a pain disorder.

Thus, in one embodiment, there is provided a dopamine stabilizing agent and an anti-depressive agent as described herein for use in the treatment of a disorder characterized by persistent and debilitating fatigue, wherein said disorder is selected from the group consisting of myalgic encephalomyelitis/chronic fatigue syndrome, fibromyalgia, mental fatigue, post stroke fatigue, Huntington's disease, Parkinson's disease, multiple sclerosis, narcolepsy, post cancer fatigue, fatigue associated with cancer with or without cytostatic treatment, depression and combinations thereof.

In one embodiment, said fatigue disorder is characterized by at least one of the conditions selected from fibromyalgia, mental fatigue, myalgic encephalomyelitis/chronic fatigue syndrome and depression. In another embodiment, said disorder is a pain disorder characterized by at least one of the conditions selected from of fibromyalgia, mental fatigue myalgic encephalomyelitis/chronic fatigue syndrome- and depression. In one embodiment, said disorder is ME/CFS. In one embodiment, said disorder is mental fatigue. In one embodiment, said disorder is depression and in another embodiment, said disorder is fibromyalgia. In one embodiment, said disorder is a combination of two or more above mentioned disorders, such as a combination selected from the group of: a combination of myalgic encephalomyelitis/ chronic fatigue syndrome and fibromyalgia; a combination of myalgic encephalomyelitis/chronic fatigue syndrome and mental fatigue; a combination of myalgic encephalomyelitis/chronic fatigue syndrome and depression; a combination of mental fatigue and depression; a combination of fibromyalgia and depression; and a combination of mental fatigue and fibromyalgia. In one embodiment, said combination is selected from: a combination of myalgic encephalomyelitis/chronic fatigue syndrome, mental fatigue and fibromyalgia; a combination of myalgic encephalomyelitis/chronic fatigue syndrome, mental fatigue and depression; a combination of myalgic encephalomyelitis/chronic fatigue syndrome, depression and fibromyalgia; a combination of depression, mental fatigue and fibromyalgia.

The skilled person will appreciate that the embodiments discussed above in relation to the first aspect of the present disclosure, are equally relevant and applicable to the second, third, fourth, fifth, sixth, seventh and eighth aspect disclosed herein. This particularly applies to embodiments relating to the identity of the dopamine stabilizing agent, the identity of the anti-depressive agent, as well as, where applicable, the mode and route of administration as well as amounts of agents administered. For the sake of brevity these will not be repeated here or will only be briefly mentioned.

In a second aspect of the present disclosure, there is provided a pharmaceutical composition comprising a dopamine stabilizing agent as described herein and an anti-depressive agent.

In one embodiment, said pharmaceutical composition further comprises at least one pharmaceutically acceptable excipient or carrier. Non-limiting examples of excipients includes diluents, disinteragrants, binders, lubricants, glidants and agents that modify release of the active agent, such as polymers. The skilled person is aware of suitable excipients and carriers.

In another embodiment, said pharmaceutical composition further comprises at least one additional active agent. In one embodiment, said additional agent is an anti-fatigue agent, such as a stimulant, for example a caffeine-based stimulant or a central nervous system stimulating agent, such as methylphenidate and various amphetamine derivatives.

In one embodiment, there is provided a pharmaceutical composition as described herein comprising an amount of dopamine stabilizing agent of approximately 0.1-45 mg, such as 0.1-5 mg, such as approximately 0.1-2 or such as approximately 1-45 mg, such as approximately 1-30 mg, such as approximately 5-30 mg, such as approximately 10-30 mg, such as 15 mg or 30 mg. In one embodiment, said amount is approximately 1-20 mg, such as approximately 5-20 mg, such as approximately 10-20 mg, such as 15 mg and in another embodiment, said amount is approximately 1-30 mg, such as approximately 15-30 mg, such as approximately 20-30 mg, such as 30 mg.

In one embodiment, said pharmaceutical composition is formulated for oral, subcutaneous, intramuscular or intravenous administration. As discussed above, it will be appreciated that non-invasive administration may be generally preferable. In one particular embodiment, said pharmaceutical composition is formulated for oral administration.

In one embodiment, wherein said pharmaceutical is formulated for oral administration, the pharmaceutical composition comprises approximately 1-45 mg, such as approximately 1-30 mg, such as approximately 5-30 mg, such as approximately 10-30 mg, such as 15 mg or 30 mg of dopamine stabilizing agent. When said pharmaceutical is formulated for subcutaneous or intramuscular administration, it may be suitable that the administered dose corresponds to approximately half of the oral dose. Thus, in one embodiment wherein said pharmaceutical is formulated for subcutaneously or intramuscularly administration, the pharmaceutical composition comprises approximately 1-30 mg, such as approximately 1-20 mg, such as approximately 15 mg, 10 mg or 8 mg.

In another embodiment, wherein said pharmaceutical composition is formulated for intravenous administration, the pharmaceutical composition comprises approximately 0.1-5 mg, such as approximately 0.1-2 mg dopamine stabilizing agent.

In one embodiment, there is provided a pharmaceutical composition formulated as a pill, tablet, capsule, dragee, liquid, gel capsule, syrup, slurry or suspension, such as a pill.

In one embodiment, there is provided a pharmaceutical composition formulated for administration once, twice or three times a day, such as once or twice a day.

In one embodiment, there is provided a pharmaceutical composition for use as described herein, said composition being formulated to provide, upon administration, a therapeutically effective blood plasma concentration of said dopamine stabilizing agent of approximately 0.1-0.7 µM, such as approximately 0.3-0.7 µM.

It is furthermore contemplated that the dopamine stabilizing agent as defined herein and an anti-depressive agent are combined into a combination kit. For example, a combination kit could comprise a dosage form of said dopamine stabilizing agent as described herein and a dosage form of an anti-depressive agent. Additionally, said kit may comprise printed matter with information and/or a suitable box container for storage of said agents.

The kit is envisioned to provide all components necessary for the administration of the dopamine stabilizing agent and the anti-depressive agent in a safe and convenient manner. For example, if the dopamine stabilizing agent and the anti-depressive agent are to be administered separately in tablet or pill form, it may be suitable for the kit to comprise an indicator for indicating that a corresponding number of tablets or pill of each types has been administered. In the instance when at least one of said agents is to be administered by injection, said kit may comprise an injection device. Thus, kits for administration by injection, such as subcutaneous, intramuscular or intravenous injection are also contemplated. Such kits may comprise said dopamine stabilizing agent and said anti-depressive agent in the same container, in form of a solution or powder or the like. Also contemplated are kits wherein said dopamine stabilizing agent and said at least one anti-depressive agent are present in separate containers. Said kits may furthermore comprise for example an injection device and/or written information.

Thus, in third aspect of the present disclosure, there is provided a combination kit comprising a dopamine agent as defined herein and an anti-depressive agent. In one embodiment, said anti-depressive agent is as defined herein.

In one embodiment of the present aspect, there is provided a combination kit wherein said dopamine stabilizing agent and said anti-depressive agent are formulated for concomitant or simultaneous administration. Kits comprising oral dosage forms are contemplated, for example kits wherein said dopamine stabilizing agent and said anti-depressive agent are present in one pill, tablet, capsule, dragee, liquid, gel capsule, syrup, slurry or suspension (or other suitable form); and kits wherein said dopamine stabilizing agent and said anti-depressive agent are present as separate pills, tablets, capsules, dragees, liquids, gel capsules, syrups, slurrys or suspensions (or other suitable forms).

In one embodiment, said combination kit is formulated to comprise an amount of dopamine stabilizing agent of approximately 0.1-45 mg such as approximately 0.1-5 mg, such as approximately 0.1-2 mg or such as approximately 1-45 mg, such as approximately 1-30 mg, such as approximately 5-30 mg, such as approximately 10-30 mg, such as 15 mg or 30 mg.

In one embodiment, said amount is approximately 1-20 mg, such as approximately 5-20 mg, such as approximately 10-20 mg, such as 15 mg and in another embodiment, said amount is approximately 1-30 mg, such as approximately 15-30 mg, such as approximately 20-30 mg, such as 30 mg.

In one embodiment, said combination kit is formulated for oral, subcutaneous, intramuscular or intravenous administration and in another embodiment, said combination kit is formulated for oral administration.

In one embodiment, said kit is formulated for oral administration and comprises approximately 1-45 mg, such as approximately 1-30 mg, such as approximately 5-30 mg, such as approximately 10-30 mg, such as 15 mg or 30 mg dopamine stabilizing agent. When said kit is formulated for subcutaneous or intramuscular administration, it may be suitable that the administered dose corresponds to approximately half of the oral dose. Thus, in one embodiment wherein said kit is formulated for subcutaneously or intramuscularly administration, the pharmaceutical composition comprises approximately 1-30 mg, such as approximately 1-20 mg, such as approximately 15 mg, 10 mg or 8 mg. In another embodiment, said kit is formulated intravenous administration and comprises approximately 0.1-5 mg, such as approximately 0.1-2 mg dopamine stabilizing agent.

In one embodiment, said combination kit is formulated for administration once, twice or three times a day, such as once or twice a day.

In one embodiment, said combination kit is formulated such that, upon administration, the therapeutically effective blood plasma concentration of said dopamine stabilizing agent is approximately 0.1-0.7 µM, such as approximately 0.3-0.7 µM.

As disclosed in the Example section of the present disclosure, the dopamine stabilizing agent or pharmaceutical composition comprising the same may be useful for the treatment of a disorder characterized by debilitating fatigue in a subject on treatment with at least one anti-depressive agent (AD). It will be appreciated that the subject may have been on ongoing treatment with an anti-depressive agent for at least 6 months, such as at least 3 months, such as at least 1 month, such as at least 2 weeks.

Thus, in a fourth aspect of the present disclosure there is provided a dopamine stabilizing agent as described herein for use in the treatment of a disorder characterized by debilitating fatigue in a subject on treatment with at least one anti-depressive agent. It will be appreciated that said subject may be suffering from a disorder characterized by debilitating fatigue as described above and that the mode and route of administration of said dopamine stabilizing agent and the amount administered may be as described above. In one embodiment of this aspect, said subject is on treatment with an anti-depressive agent as described above.

In an additional aspect of the present disclosure, there is provided the use of a dopamine stabilizing agent as defined herein and an anti-depressive agent, for the manufacture of a medicament for the treatment a disorder characterized by persistent and debilitating fatigue, such as a disorder disclosed herein. In one embodiment, said anti-depressive agent is as defined herein.

In a related aspect, there is provided the use of a dopamine stabilizing agent as defined herein, for the manufacture of a medicament for the treatment a disorder characterized by debilitating fatigue in a subject on treatment with an anti-depressive agent, such as in a subject on treatment with an anti-depressive agent as described herein. It will also be appreciated that said disorder characterized by debilitating fatigue may be any one of the disorders disclosed herein.

In the seventh aspect of the present disclosure, there is provided a method for the treatment of a disorder characterized by persistent and debilitating fatigue, wherein the method comprises administering to a subject in need thereof a therapeutically effective dose of a dopamine stabilizing agent, wherein said subject is on treatment with an anti-depressive agent and wherein said dopamine stabilizing agent is as defined above. In one embodiment, said subject in on treatment with an anti-depressive agent selected from the anti-depressive agents defined above.

In a related, eighth aspect of the present disclosure, there is provided a method of treatment of a disorder characterized by persistent and debilitating fatigue, the method comprising co-administration, to a subject in need thereof, of a therapeutically effective dose of a dopamine stabilizing agent as defined above and a therapeutically effective dose of an anti-depressive agent. In one embodiment, said anti-depressive agent may be selected from the anti-depressive agents defined above. It will be appreciated, that in the context of the eighth aspect of the present disclosure, said co-administration may be concomitant or simultaneous, such as concomitant administration within less than 24 hours, such as within less than 12 hours, such as within less than 6 hours, such as within less than 1 hour or such as simultaneous co-administration.

In embodiments of the seventh and eight aspects of the present disclosure, the disorder characterized by debilitating fatigue may be as described above and the mode and route of administration as well as amount administrated may be as described above.

Measurements of Clinical Outcome

As described in the Example section to follow, the clinical outcome of administration of a dopamine stabilizing agent and an anti-depressive agent to a subject suffering from a disorder as described herein or of administration of a dopamine stabilizing agent as described herein to a subject on treatment with an anti-depressive agent, may be evaluated by the following tests and questionnaires. The skilled person is aware of the applicability of these test for the evaluation of fatigue and depression related symptoms.

As used herein, the term "Clinical Global Impression" (CGI) refers to a rating scale commonly used to measure symptom severity, treatment response and the efficacy of treatments in treatment studies of patients with mental disorders (Guy W: Clinical Global Impressions (CGI) Scale. Modified From: Rush J, et al.: Psychiatric Measures, APA, Washington D.C., 2000).

As used herein "Clinical Global Impression of Change" (CGI-C) (also known as Clinical Global Impression—Improvement (CGI-I)) scale is a 7 point scale that requires the clinician to assess how much the patient's illness has improved or worsened relative to a baseline state at the beginning of the intervention. The ratings are as follows: 1, very much improved; 2, much improved; 3, minimally improved; 4, no change; 5, minimally worse; 6, much worse; or 7, very much worse.

As used herein, the term "MFS" refers to a the mental fatigue self-assessment questionnaire (Johansson B et al (2010) Brain Injury 2010; 24:2-12).

Additionally, the clinical outcome of the treatment may be evaluated using the FF-scale, The Beck/BDI scale, VAS pain scale and by neuropsychological tests.

As used herein, the term "FF-scale" or "FF" refers to the FibroFatigue scale also known as the fibromyalgia and chronic fatigue syndrome rating scale described in by Zachrisson and coworkers (Zachrisson O, et al, (2002) J Psychosom Res Jun; 52(6):501-9). The FibroFatigue scale is an observer's rating scale with 12 items measuring pain, muscular tension, fatigue, concentration difficulties, failing memory, irritability, sadness, sleep disturbances, and autonomic disturbances and irritable bowel, headache and subjective experience of infection.

As used herein, the terms "Beck/BDI scale" and "BD" refers to the Beck Depression Inventory created by Aaron T. Beck (Beck A T et al., (1961) Arch. Gen. Psychiatry 4(6): 561-71). It is a 21-question multiple-choice self-report inventory and one of the most widely used instruments for measuring the severity of depression. The BDI questionnaire is designed for individuals aged 13 and over, and is composed of items relating to symptoms of depression such as hopelessness and irritability, cognitions such as guilt or feelings of being punished, as well as physical symptoms such as fatigue, weight loss, and lack of interest in sex.

As used herein, the term "VAS pain scale" refers to the visual analog scale for measuring a patient's pain intensity or other features. The VAS scale is a psychometric response scale and is often used in questionnaires. It is a measurement instrument for subjective characteristics or attitudes that cannot be directly measured. When responding to a VAS item, respondents specify their level of agreement to a statement by indicating a position along a continuous line between two end-points.

As used herein, the term "neuropsychological tests" refers to tests designed to measure unobserved constructs, also known as latent variables. Psychological tests are typically, but not necessarily, a series of tasks or problems that the respondent has to solve and measure a respondent's maximum performance. The neuropsychological tests employed in this study are described in Example 6.

Statistical Analysis

This study employs statistical evaluations of obtained data. The skilled person is aware of and knows how to employ the tests used herein. Any deviations from standard calculations procedures are explained in the Example section of the disclosure. Briefly, the statistics test employed herein are as follows:

The Mann-Whitney U test (also called the Mann-Whitney-Wilcoxon (MWW), Wilcoxon rank-sum test (WRS), or Wilcoxon-Mann-Whitney test) is a nonparametric test of the null hypothesis that two populations are the same against an alternative hypothesis, especially that a particular population tends to have larger values than the other.

The 2-way interaction analysis (2-way analysis of variance (ANOVA)) is a test that examines the influence of two different categorical independent variables on one continuous dependent variable. The two-way ANOVA not only aims at assessing the main effect of each independent variable but also at assessing if there is any interaction between them.

The 3-way interaction analysis (3-way analysis of variance (ANOVA)) is a test that examines if there is a 2-way interaction that varies across levels of a third variable.

Spearman's rank correlation coefficient is a nonparametric measure of statistical dependence between two variables. It assesses how well the relationship between two variables can be described using a monotonic function. If there are no repeated data values, a perfect Spearman correlation of +1 or −1 occurs when each of the variables is a perfect monotone function of the other.

While the invention has been described with reference to various exemplary aspects and embodiments, it will be understood by those skilled in the art that various changes may be made and equivalents may be substituted for elements thereof without departing from the scope of the invention. Therefore, it is intended that the invention not be limited to any particular embodiment contemplated, but that the invention will include all embodiments falling within the scope of the appended claims.

BRIEF DESCRIPTION OF THE FIGURES

FIG. 1 is an overview of the clinical phase II study. In each of the columns Screening, Random and Check 1-4 it is indicated if it was performed on site or not, when it was performed in relation to the start of the study and what tests and analysis were performed.

FIG. 2 is a summary of the demographic and baseline characteristics of the patient cohort. The quantity or mean (standard deviation (SD)) is shown.

EXAMPLES

Summary

Figure 3:
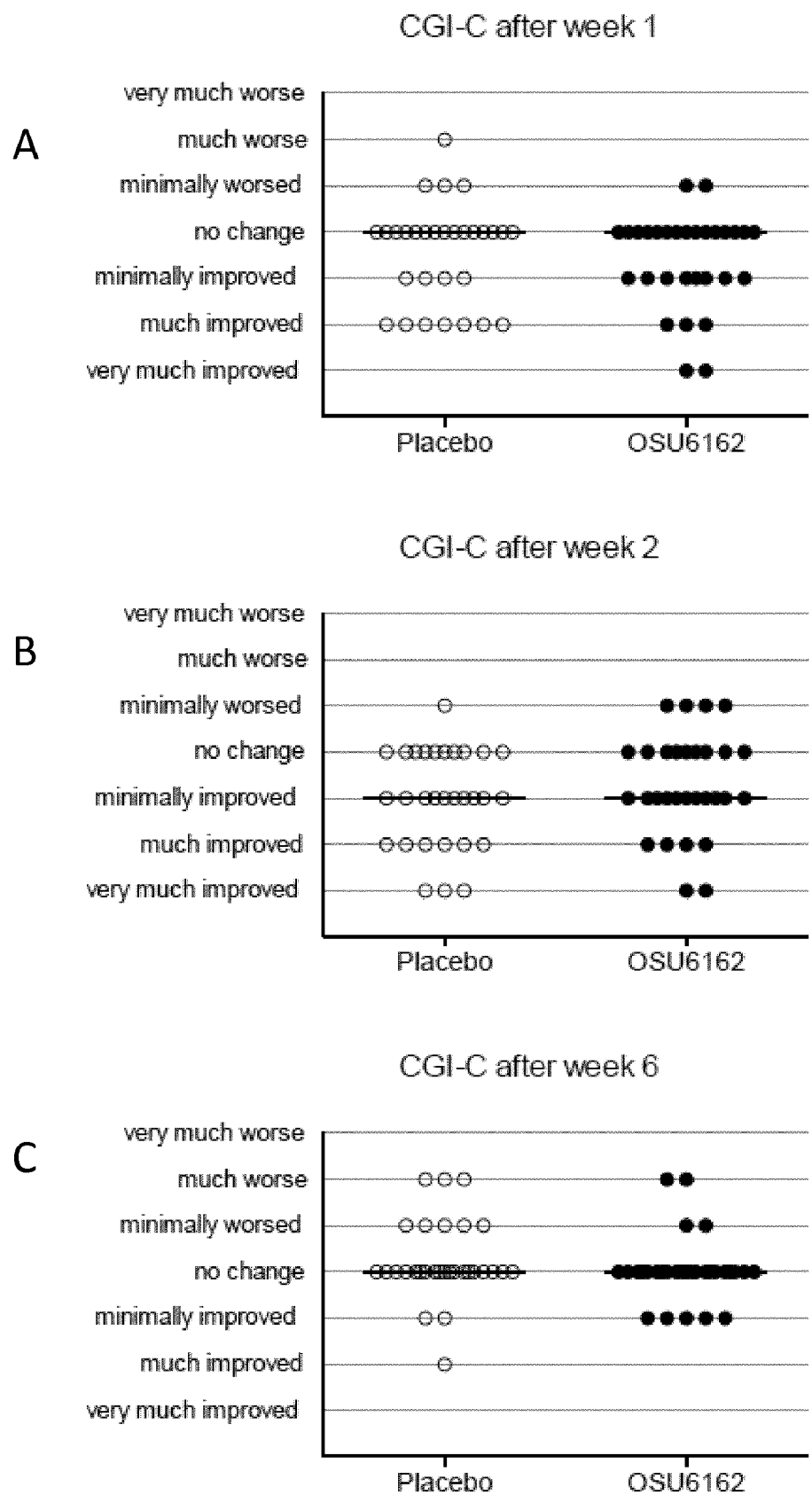
FIGS. 3A, B and C show the CGI-C values in the placebo treated patient population (empty circle) and the OSU6162 treated patient population (filled circle) after 1 week of treatment, after 2 weeks of treatment and after 6 weeks, respectively. Each circle represents one patient.

The following Examples disclose the outcome of a phase II clinical study aiming at investigating the therapeutic effects of the S enatiomer of (3S)-3-[3-(methylsulfonyl)-phenyl]-1-propylpiperidine hydrochloride (herein interchangeably referred to as OSU6162 and (−)-OSU6162) for the treatment of ME/CFS as measured by mental fatigue self-assessment (MFS) questionnaire and Clinical Global Impression of Change (CGI-C) as well as some other additional parameters. The study was performed as a double-blind placebo-controlled study, wherein half of the patients were administered the active drug and the other half were administered placebo. Importantly, the study demonstrated significantly improved outcomes in a subgroup of patient who were treated with an anti-depressive agent compared to the corresponding sub-group being treated by OSU6162 without any anti-depressive treatment.

Example 1

Description of the Clinical Phase II Study

The study was performed in accordance with the current version of the declaration of Helsinki (52nd WMA General Assembly, Edinburgh, Scotland, October 2000) and in compliance with the requirements of the Medical Products Agency of Sweden. The trial was conducted in agreement with the International Conference on Harmonisation (ICH) guidelines on Good Clinical Practise (GCP). All patients provided written informed consent to participate in the study prior to being screened.

FIG. 1 shows an overview of the study performed. The overview shows when, where and what data was collected from the patients at each instance.

Example 2

Selection of the Study Population

Inclusion Criteria

The Fukuda criteria and the International Consensus Criteria (ICC) for diagnosis of ME/CFS were applied as inclusion criteria in this study.

The ICC for the diagnosis ME was presented in the Journal of Internal Medicine (International Consensus Criteria, ICC, Carruthers et al (2011) Volume 270, Issue 4 Pages 295-400) and are an update of the previously used Fukuda (Fukuda et al (1994) Annals of Internal Medicine; 121:953-959) and Canadian Criteria (Carruthers et al (2003) Journal of Chronic Fatigue Syndrome 11(1):7-115).

Patient Population

Patients were recruited from the ambulatory service at the Gottfries Clinic AB. 79 patient were screened and 17 did not meet the inclusion criteria for various reason (significant pathological lab finding and not permitted concomitant medication: 1 patient; significant pathological lab findings: 4 patients; depression: 3 patients; high blood pressure: 3 patients; diagnostic criteria ME not fulfilled: 1 patient; concomitant medications: 2 patients; post commotio cerebri: 1 patient; pregnancy: 1 patient; cancelation by patient due to night work: 1 patient; drop-out: 1 patient; technical mistake with study drug by research nurse: 2 patients) resulting in a group of 62 patients which were randomized.

Exclusion Criteria

Medication that is known/judged not to interfere with OSU6162 was permitted. Medications which were not permitted were anti-epileptics or antipsychotics.

Patients with active substance abuse, pregnant women, women of childbearing age not on contraceptives and patients with abnormal laboratory parameters (e.g. Hb, white blood cells count, electrolytes, tests of liver and kidney functions, TSH, T4, B12, folic acid) judged to be of clinical significance were not accepted.

Unstable therapies were not allowed but stable therapies were allowed. A stable therapy is defined as having started at least 6 months before the study and continued to be unchanged during the study period. Examples of such therapies are treatments with anti-depressants. Other stable therapies with hypnotics and anxiolytics were also allowed if they were given at doses recommended by the manufacturers.

Furthermore, analgesics such as NSAIDs, e.g. acetyl salicylic acid, paracetamol and duloxetine were permitted as well as stable anti-hypertensive therapy. Acute or chronic medications for other medical conditions were allowed based on clinical judgment.

Occasional use of over-the-counter (OTC) medications was allowed at the investigator's discretion.

All concomitant medications, whether OTC or prescription, were noted.

Withdrawal of Patients from Therapy or Assessment

Patients were free to withdraw from the study at any time without giving a reason. Patients were advised that a request to withdraw from the study, at any time during the trial, would have no negative consequences. The investigators could also withdraw patients from the trial if they deemed it appropriate for safety or ethical reasons or if they considered further participation in the study detrimental to the well-being of the patient. Patients who withdrew or were withdrawn underwent a final evaluation as soon as possible.

Any adverse event (AE) or serious adverse event (SAE) were reported and to the Ethics committee according to regulations.

To summarize, 62 patient were included in the study population and 1 patient withdrew from the study (Table 1). One patient in the OSU6162 treatment group, who lacked detectable levels of plasma OSU6162 was not included in the analysis.

TABLE 1

Disposition of patients. Number of patients is indicated. Group A are patients who received OSU6162 and group B are patients who received the placebo control.

|  | Group A | Group B | Total |
| --- | --- | --- | --- |
| Enrolled (received at least one tablet) | 31 | 31 | 62 |
| Completed (Withdrawn) | 31 | 30 (1*) | 61 |

*Patient withdrawn from study according to patient wish due to urinary tract infection.

Example 3

Treatment with OSU6162

The study was performed as a double-blinded placebo-controlled study, where half of the patients received the active drug and the other half received placebo. Circular coated tablets for oral use of 15 mg and matching placebos was used. The tablets were administered by research nurses at the study site.

Description of Investigational Products

The investigated substance is the S enantiomer with the chemical name (S)-3-[3-(methylsulfonyl) phenyl]-1-propylpiperidine hydrochloride, referred herein to as OSU6162. The substance is a white powder with a melting point of 177-182° C. and water solubility of >2000 mg/ml.

OSU6162 belongs to a group of compounds called dopaminergic stabilizers which modulate dopaminergic transmission.

Method of Assigning Patients to Treatment Groups

Randomization of patients participating in the study was done by an external agent. The randomization procedure was performed in agreement with CONSORT (Consolidated Standards of Reporting Trials) guidelines.

Doses for Use in the Study

Tablets were delivered in sets of 20 packages of tablets containing 10 with active substance and 10 with placebo. Procedures were taken to guarantee blinding and the code was kept in a locked drawer at the study site. All persons dealing with the patients were blinded towards active drug or placebo.

The tablets were circular coated tablets for oral use containing 15 mg OSU6162. Matching placebos were used. The start dose was 15 mg OSU6162 twice daily (before breakfast and lunch) during 1 week with dose increase up to 30 mg twice daily during the following week.

The dosage was individually flexible which means that if a patient experienced adverse events, the dose was reduced with 15 mg OSU6162 (one tablet), thus continuing with 15 mg once daily taken in the morning.

Total period for active drug treatment for each participant was two weeks.

Treatment Compliance

All study treatment was administered by the study investigator or designated member of staff. To ensure drug accountability the investigator or designated deputy maintained accurate records of the dates and amounts of drug received, to whom it was dispensed and accounts of any supplies which were accidentally or deliberately destroyed; these details were recorded on a drug accountability form. All unused clinical supplies and the drug accountability forms were returned to the sponsor at the end of the study.

Efficacy and Safety Variables

Efficacy was measured according to ratings using the self-assessment questionnaire for mental fatigue and related symptoms (MFS) after neurological disorders and injuries (Johansson et al, supra). Another primary endpoint was the result of the rating by the Clinical Global Impression of Change (Guy, supra), which rating was made by the doctor in charge of the patient. CGI-C scores range from 1 (very much improved) through to 7 (very much worse).

Additionally, the clinical effect was evaluated using the FF-scale, The Beck/BDI scale, VAS pain scale and with neuropsychological tests.

Patient safety was measured by ECG and was subject to clinical investigation of vital signs and laboratory tests.

FIG. 1 provides a summary of the assessment and analysis done at each of the visits to the clinic.

Example 4

Outcome of Treatment with OSU6162 Alone or Concomitant with Anti-Depressant Treatment In this Example, outcome variables of the treatment with OSU6162 alone or concomitant with anti-depressant treatment were evaluated.

Overview of Patient Population

Data from 60 patients was analyzed, whereof 30 received the placebo control and 30 received treatment with OSU6162. In each group, 11 patients were on treatment with a stable dose of an anti-depressive agent (AD). Table 2 summaries the antidepressant agents taken by patients included in the study. FIG. 2 shows an overview of the demographic distribution of the patient population, as well as the base line characteristics of the patients at the start of the study (week 0). No significant difference was observed between the placebo and the OSU6162 group and no significant difference was observed between the patients on anti-depressant treatment and the patients not on antidepressant treatment. Thus, it was concluded that the randomization was satisfactory.

TABLE 2

Summary of anti-depressive agents (AD) taken by patients concomitantly with OSU6162.

| Anti-depressive agent (AD) | Type of anti-depressive agent | Number of patients |
| --- | --- | --- |
| Escitalopram, Citalopram | selective serotonin reuptake inhibitor | 8 |
| Venlafaxine | serotonin-norepinephrine reuptake inhibitor | 4 |
| Sertaline | selective serotonin reuptake inhibitor | 3 |
| Flouxetine | selective serotonin reuptake inhibitor | 1 |
| Paroxetine | selective serotonin reuptake inhibitor | 1 |
| Duloxetine | serotonin-norepinephrine reuptake inhibitor | 10 |
| Amitriptyline | tricyclic antidepressant | 10 |

Clinical Global Impression of Change

Clinical Global Impression of Change (CGI-C) was evaluated by the clinician for each patient.

After one week of treatment, 13 of 30 (43%) OSU6162-treated patients exhibited improved CGI-C values and 11 of 30 (37%) placebo-treated patients exhibited improved CGI-C values. After two weeks, 17 of 30 (57%) OSU6162-treated patients exhibited improved CGI-C values and 19 of 30 (63%) placebo-treated patients exhibited improved CGI-C values. Thus, no significant difference in CGI-C was observed the between treatment groups for the entire patient population (FIG. 3).

Figure 4:
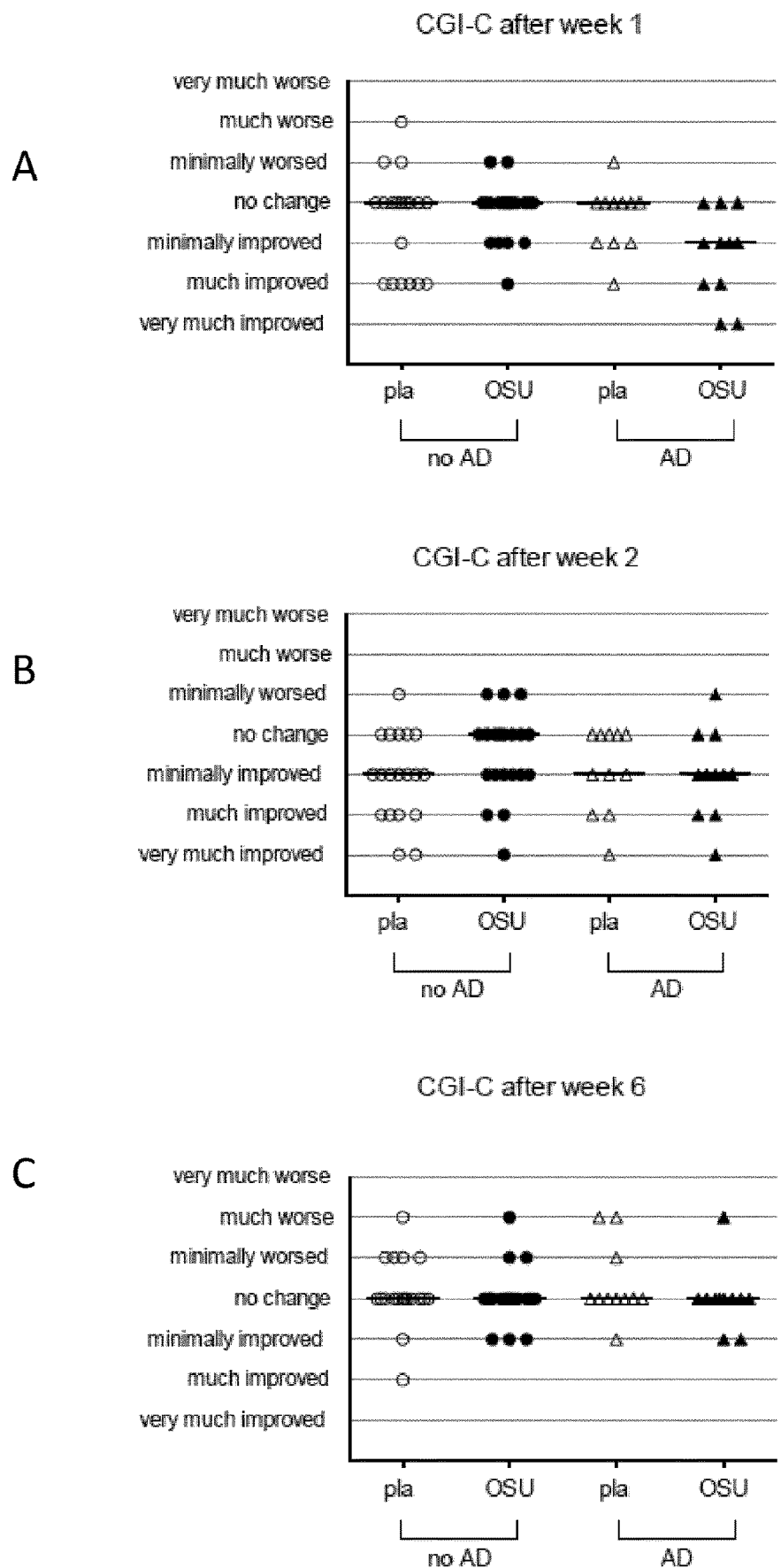
FIGS. 4A, B and C show the CGI-C values in the placebo treated patient population (empty circle) and the OSU6162 treated patient population (filled circle) not on treatment with an anti-depressive agent (no AD) as well as the CGI-C values in the placebo treated patient population (empty circle) and the OSU6162 treated patient population on treatment with (filled circle) anti-depressive agent (AD). Values are shown after 1 week of treatment, after 2 weeks of treatment and after 6 weeks, respectively. Each circle represents one patient.

Importantly, in the subgroup receiving concomitant anti-depressant treatment (for the treatment of depression), there was a clear tendency after one week for a greater improvement among patients treated with OSU6162 than among those treated with placebo (Mann-Whitney U-test: p=0.0524) (FIG. 4).

2-Way Interaction Analysis

In order to investigate if the was any interaction between two different, categorical independent variables on the treatment outcome, 2-way ANOVA analysis was performed.

2-way ANOVA analysis did not show any interactions between treatment and time, i.e. the effect of OSU6162 vs. placebo did not differ over time.

For MFS there was a borderline significant trend to an overall group difference between OSU6162 and placebo treatment ($F_{1,60}$=3.997, p=0.050 (FIG. 4B). None of the other outcome targets (FF (FIG. 4A), BDI (FIG. 4C) and neuropsychological tests) showed any main effect of treatment.

Consistently, all outcome targets (FF, MFS, BDI, pain VAS and neuropsychological tests) showed main effects of time, i.e. regardless of treatment there were improvements in these scale scores over time (p<0.0001). Compared to week 0, FF and MFS scores were improved after both week 1 (week 0-1) and week 2 (week 0-2) but not at follow-up after 6 weeks. BDI score was significantly improved after week 2 compared to week 0. Statistical analysis was performed using IBM SPSS Statistics. Version 20 software and is presented below:

FF (week 0-1): $t_{180}$=−2.914, p=0.004;
FF (week 0-2): $t_{180}$=−4.446; p=0.00002;
MFS (week 0-1): $t_{180}$=−2.961; p=0.003;
MFS (week 0-2): $t_{180}$=−4.649; p<0.00001; and
BDI (week 0-2): $t_{180}$=−2.300; p=0.023.

3-Way Interaction Analysis

To examine the effect of treatment and concomitant use of an antidepressant, antidepressant was included as a fixed factor in the analyses. This resulted in improved models and reduced level of unexplained variance. The antidepressant factor included two levels: 1) patients on stable antidepressant therapy to treat depression (i. e. since at least 6 months before start of the trial) and 2) patients who did not receive medication to treat depression. Outcome targets FF, MFS and BDI were measured.

Figure 5:
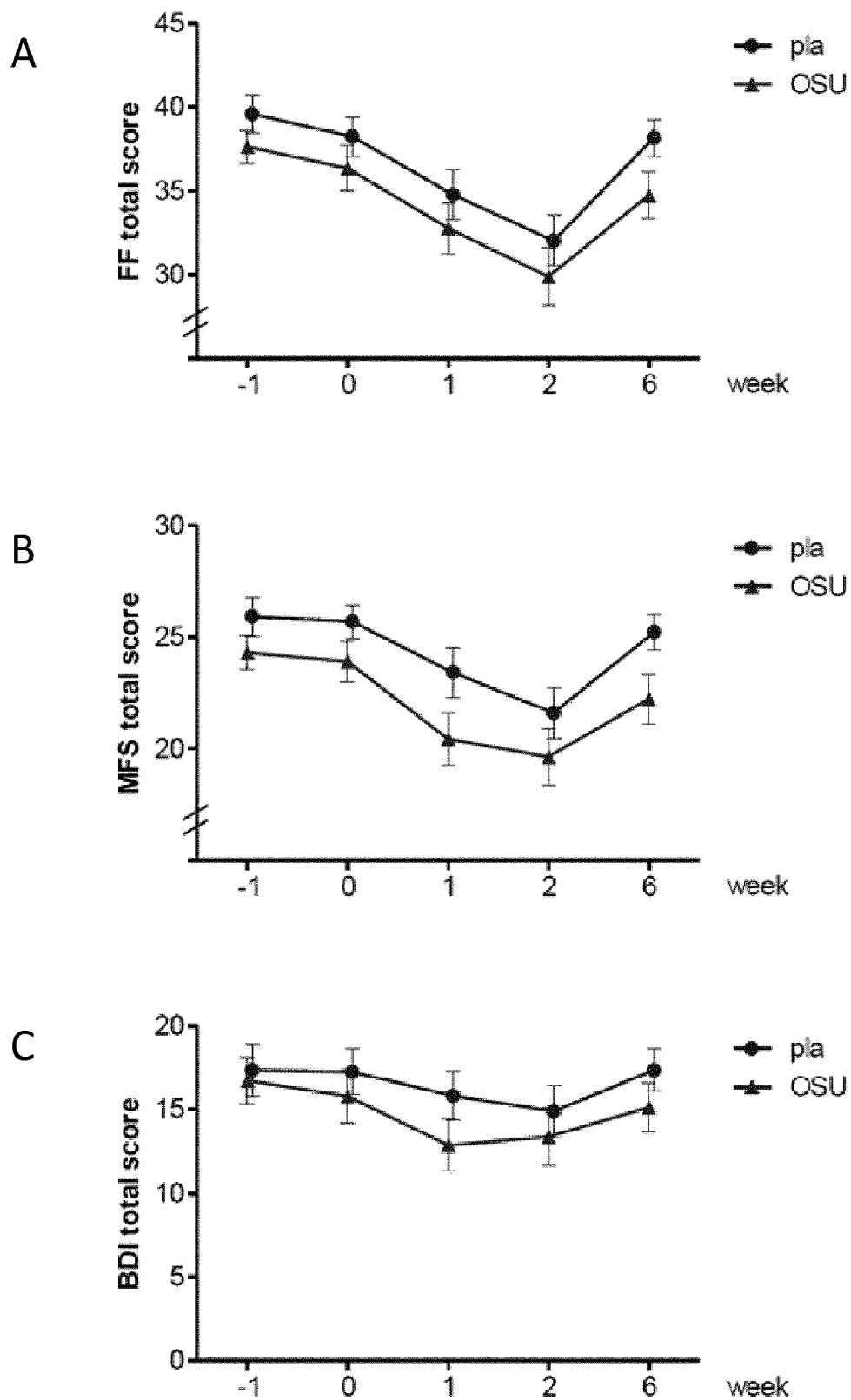
FIGS. 5A, B and C show the FF total score, MFS total score and the BDI total score, respectively, as measured at the time points of the study in the placebo treated patient group (circle) and the OSU6162 treated patient group (triangle). The x-axis shows the time points in weeks and the y-axis shows the total score.

Similarly to the 2-way interaction analysis there were no significant interactions between treatment and time, nor main effect of treatments. However, the tendency to an overall difference between OSU6162 and placebo treatment on MFS remained ($F_{1,60}$=3.578, p=0.063) and FF, MFS and BDI showed main effects of time (p<0.0001; FIGS. 5A, B and E).

Importantly, it was unexpectedly observed that there were statistically significant 3-way interactions between the effects of treatment with OSU6162 and antidepressant over time (week*treatm*antidepr) for FF ($F_{3,180}$=6.785, p=0.0002) (dashed line, empty triangle, FIG. 6A) and MFS ($F_{3,180}$=2.755 p=0.044) (dashed line, empty triangle, FIG. 6B). The significant interactions were found between week 1 and inclusion for FF and MFS. Statistical analysis was performed using IBM SPSS Statistics. Version 20 software and is presented below:

FF (week 0-1) $t_{180}$=−3.491, p=0.001;
MFS (week 0-1) $t_{180}$=−2.254, p=0.025;
FF (week 0-2) $t_{180}$=−1.709, p=0.089; and
MFS (week 0-2) $t_{180}$=−1.914, p=0.057.

These significant 3-way interactions were followed by post hoc t-test comparisons. Changes from week 0 were used to evaluate the effect of OSU6162 treatment in patients on stable antidepressant therapy and in patients who were not on treatment for depression, respectively. Significant improvements after one week of treatment were observed on the FF- and MFS-scales in the OSU6162 treated patient group on antidepressant therapy compared to placebo treated patient group on antidepressant therapy [FF ($F_{1,56}$=6.320; p=0.015); 95% confidence interval for the difference: −7.23 (−13.1 to −1.48) and MFS (F1,$_{56}$=5.915; p=0.018); 95% CI for the difference: −4.82 (−8.79 to −0.85); Bonferroni correction for multiple comparisons was applied]. No difference between OSU6162 treated and placebo treated patients on any scale was observed in the groups of patients who were not on antidepressant therapy.

In summary, the above analyses show that OSU6162 was, after one week of treatment, more efficient than placebo in improving symptoms according to the FF- and MFS-scales in patients on stable antidepressant therapy.

Example 5

Measurements of OSU6162 Concentration in Blood Plasma

Next, the concentration of OSU6162 in blood plasma was measured and analyzed for correlations with time and changes in FF, MFS and BDI score.

Results of OSU6162 Plasma Concentration Measurements

Plasma concentrations of OSU6162 were measured in 30 patients who received placebo and in 31 patients who received OSU6162. The blood sample was drawn in the morning after the tablet was taken—the time of the tablet intake was noted and reported to the clinic by the patient. The blood sample was taken at minimum 65 and at maximum 180 minutes after tablet intake. The mean time was 123 minutes and the standard deviation 33 minutes.

As expected, no concentration of OSU6162 was detected in placebo-treated patients. In one patient who received OSU6162 treatment there was no detectable level of OSU6162, hence this patient was omitted from the statistical analyses.

A correlation analysis (Spearman rank correlation) was made between plasma concentration of OSU6162 and time elapsed in minutes between intake of tablet and blood sampling. No significant correlation was found.

Figure 6:
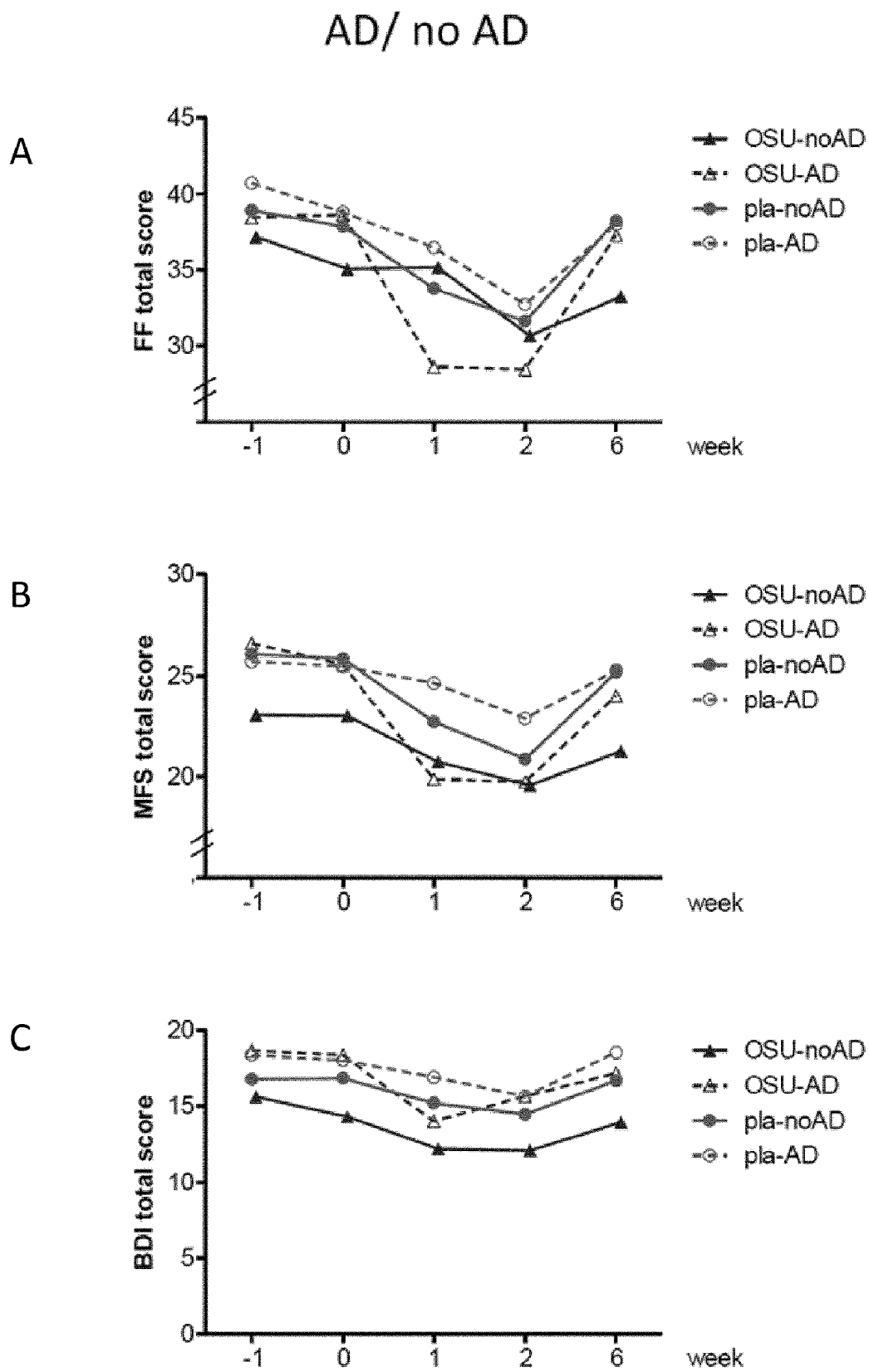
FIGS. 6A, B and C show the FF total score, MFS total score and the BDI total score, respectively, as measured at the time points of the study in the placebo treated patient group not on AD treatment (circle, solid line); the OSU6162 treated patient group not on AD treatment (triangle, solid line); the placebo treated patient group on AD treatment (circle, dashed line); and the OSU6162 treated patient group on AD treatment (triangle, dashed line). The x-axis shows the time points in weeks and the y-axis shows the total score. Group means and SEM for OSU6162 and placebo groups on AD treatment and not on AD treatment are shown.
Figure 7:
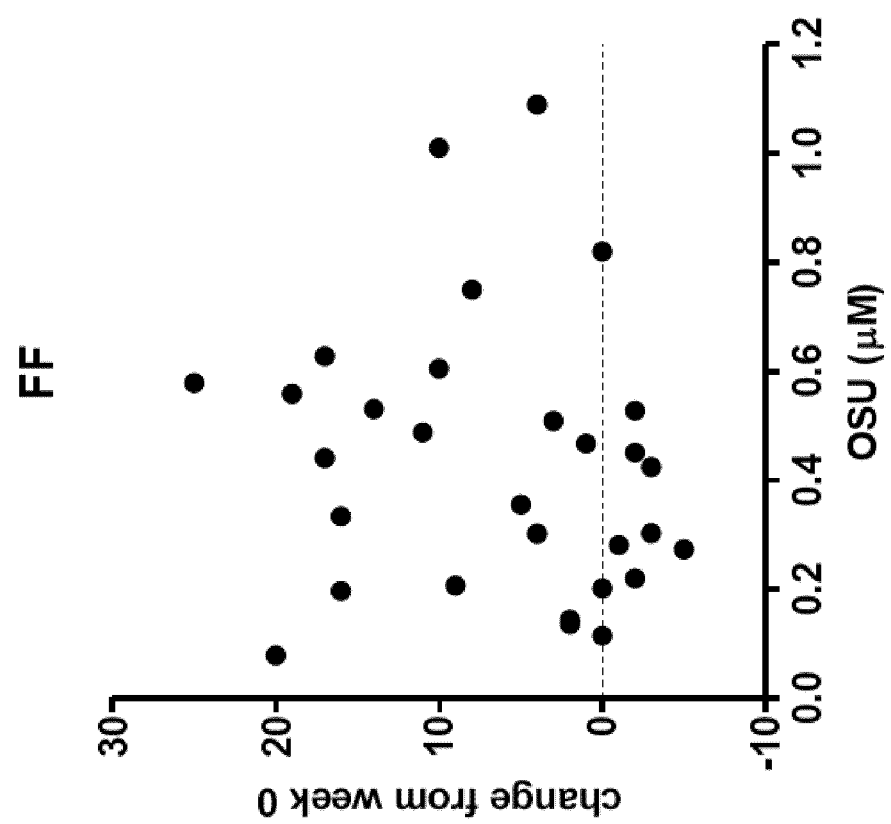
FIG. 7 is a scatter plot, wherein each dot represents a patient sample. The change in FF total score from week 0 is shown on the y-axis and the plasma concentration of OSU6162 in $\mu M$ is shown on the x-axis.
Figure 8:
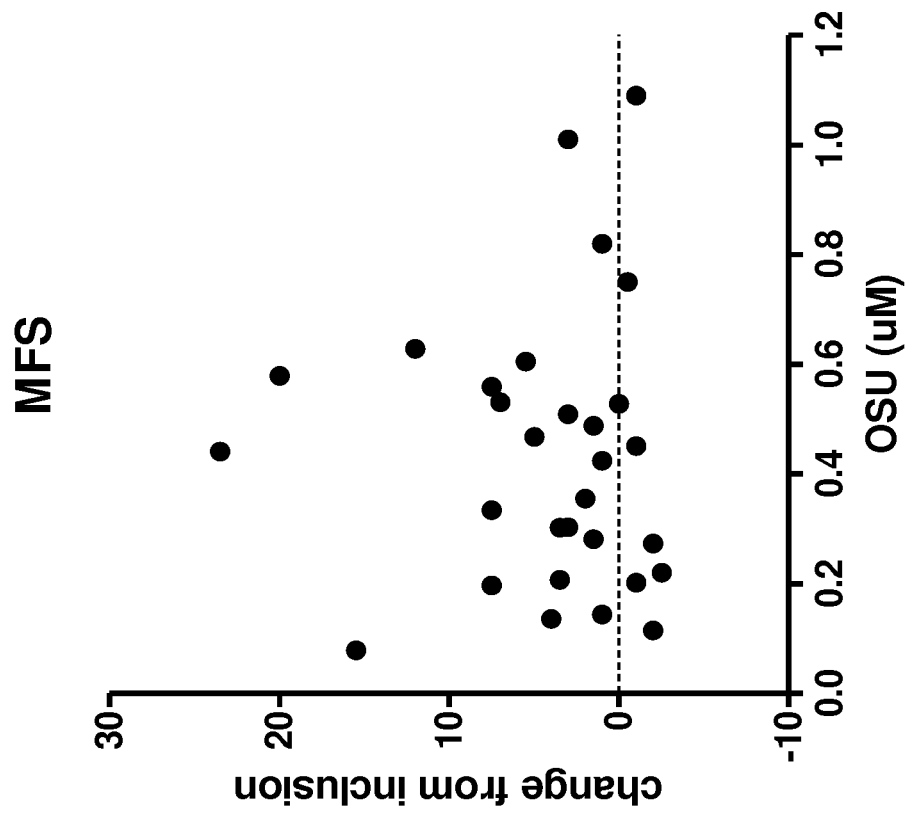
FIG. 8 is a scatter plot, wherein each dot represents a patient sample. The change in MFS total score from week 0 is shown on the y-axis and the plasma concentration of OSU6162 in $\mu M$ is shown on the x-axis.
Figure 9:
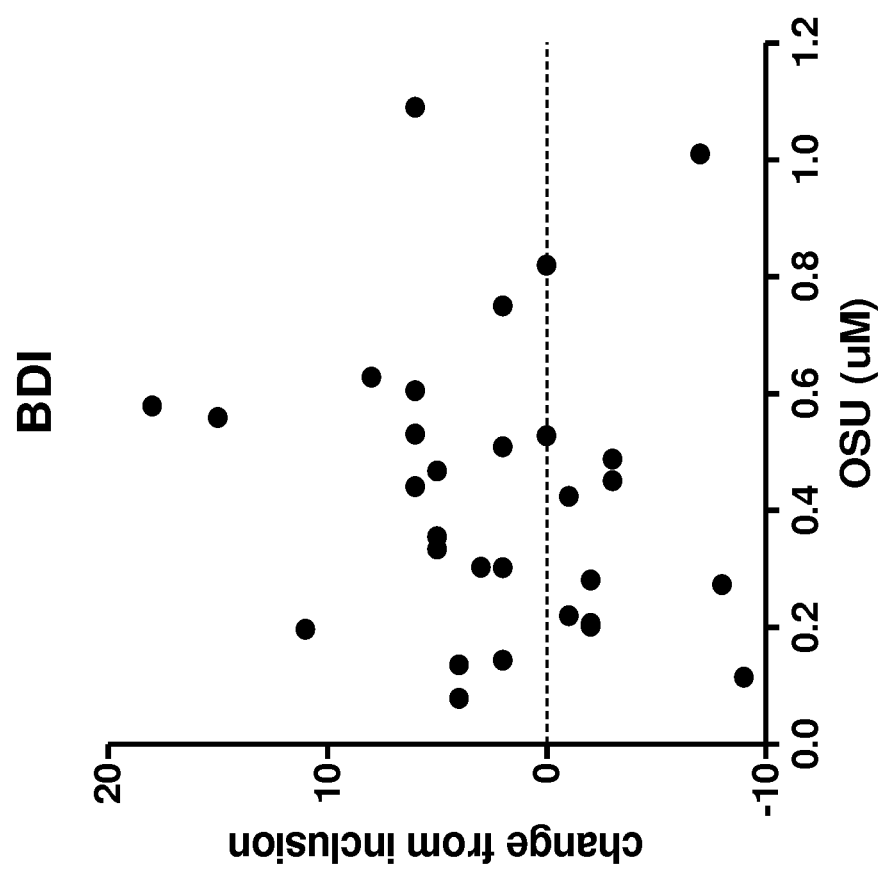
FIG. 9 is a scatter plot, wherein each dot represents a patient sample. The change in BDI total score from week 0 is shown on the y-axis and the plasma concentration of OSU6162 in $\mu M$ is shown on the x-axis.

Correlations Between OSU6162 Concentration in Plasma and Change in FF, MFS and BDI Score In order to analyze the relationship between the treatment outcome and the concentration of OSU6162 in blood plasma, OSU6162 concentrations in patients measured after week 2 were plotted against change in FF, MFS and BDI score (FIGS. 6, 7 and 8). It was noted that there seems to be a therapeutic optimum around 0.3-0.7 μM as concentrations above 0.7 μM do not seem to lead to any further improvement.

Correlation analyses (Spearman rank correlation) showed a significant correlation between OSU6162 concentration and change in FF, MFS and BDI score, respectively, within the concentration interval 0.1-0.7 μM. Statistical analysis was performed using IBM SPSS Statistics. Version 20 software and is presented below:

FF: Rs=0.418, p=0.038;
MFS: Rs=0.466, p=0.019; and
BDI: Rs=0.491 p=0.013.

Example 6

Neuropsychological Testing of Cognitive Functioning

Next, patients were evaluated using a neuropsychological test. 61 patients were included in a neuropsychological examination. All subjects were tested once in connection with the randomization with the BNIS neuropsychological screening test. 20-30 minutes was required for this test. With the purpose of measuring the cognitive effects of the OSU6162 treatment six more tests were distributed at a first occasion before the initiation of treatment and at a second occasion after the treatment was completed. These tests required 20 minutes each. All tests were performed by a neuropsychologist.

Below follows a description of the tests performed and the results thereof:

Barrow Neurological Institute Screen for Higher Cerebral Functions

Barrow Neurological Institute Screen for Higher Cerebral Functions (BNIS) is a screening test constructed to quantitatively and qualitatively reflect the outcome of a range of higher cerebral functions. The three initial items are pre-screening items where arousal level, basic communication skills and level of cooperation are assessed (a maximum score of 9) to decide whether the status of the patients allows further testing. At least two points in each item are required. The BNIS contains the following domains: speech and language (maximum score 15), orientation (maximum score 3), attention/concentration (maximum score 3), visual and visual spatial problem solving (maximum score 8), learning and memory (maximum score 7), affect (maximum score 4) and awareness vs. performance (maximum score 1). The test provides a total score=50 of overall cognitive functioning and subscale scores. A score less than 47 indicates brain dysfunction.

Results:

Table 3 show the results from the BNIS test for the OSU6162 treated patient group and for the placebo treated patient group. No significant difference was observed between the groups.

TABLE 3

Results from BNIS test.

| BNIS | OSU6162 | Placebo |
|---|---|---|
| Mean | 45.2 | 44.5 |
| STDEV | 3.5 | 2.6 |
| Min | 33 | 39 |
| Max | 50 | 48 |

Coding Test

The Coding test is a subtest from WAIS, Wechsler Adult Intelligence Scale and measures the processing speed. The performance reflects abilities such as visual-motor coordination, motor and mental speed and working memory. It requires the subject to copy, as quickly and correctly as possible, nine symbols, one by one in 93 boxes, placed below each number. The symbol connected with the numbers is available. The score is the number of symbols registered within 90 seconds.

Results:

Table 4 shows the results from the Coding test before and after treatment from patients treated with OSU6162 and patients treated with placebo. No significant differences were observed between the groups.

TABLE 4

Results from Coding test.

| | CODING | | | | | |
|---|---|---|---|---|---|---|
| | OSU6162 Before | OSU6162 After | Difference | Placebo Before | Placebo After | Difference |
| MEAN | 51.42 | 56.29 | | 49.07 | 56.17 | |
| MEDIAN | 51 | 56 | | 50 | 58 | |
| STDEV | 12.32 | 12.45 | | 9.48 | 10.24 | |

TABLE 4-continued

Results from Coding test.

| | CODING | | | | | |
|---|---|---|---|---|---|---|
| | OSU6162 Before | OSU6162 After | Difference | Placebo Before | Placebo After | Difference |
| MIN | 31 | 37 | | 28 | 36 | |
| MAX | 80 | 93 | | 68 | 82 | |
| Increased mean | | | 5 | | | 7 |

Trail Making Test A

Trail making test A (TMT A) requires the subject to draw a line as quickly as possible connecting a series of numbers. It is a time-based measure of attention, where time and quality are noted and requires motor effectiveness, visual scanning, speed and flexibility. The test has a high sensitivity for brain dysfunction.

Results:

Table 5 shows the results from the TMT A before and after treatment from patients treated with OSU6162 and patients treated with placebo. No significant differences were observed between the groups.

TABLE 5

Results from TMT A.

| TMT A | Before | After | Difference |
|---|---|---|---|
| | OSU6162 | | |
| MEAN | 33.4 | 28.5 | 10 |
| MEDIAN | 32 | 29 | |
| STDEV | 10.8 | 7.8 | |
| MIN | 16 | 15 | |
| MAX | 57 | 48 | |
| | Placebo | | |
| MEDEL | 32.7 | 28 | 7 |
| MEDIAN | 32 | 26 | |
| STDAV | 10.7 | 9.5 | |
| MIN | 15 | 13 | |
| MAX | 55 | 57 | |

Trail Making Test B

Trail making test B (TMT B) demonstrates the effectiveness of visual scanning and measures alternating attention. The subject follows a mental track and the test requires the ability to handle more than one stimulus at a time, as well as flexibility in shifting between different activities. It has a high sensitivity for brain dysfunction and is regarded to be related to prefrontal functioning.

Results:

Table 6 shows the results from the TMT B before and after treatment from patients treated with OSU6162 and patients treated with placebo. No significant differences were observed between the groups.

TABLE 6

Results from TMT B.

| TMT B | Before | After | Difference |
|---|---|---|---|
| | OSU6162 | | |
| MEAN | 71.7 | 61.2 | 10 |
| MEDIAN | 32 | 29 | |
| STDEV | 20.8 | 21.8 | |

TABLE 6-continued

Results from TMT B.

| TMT B | Before | After | Difference |
|---|---|---|---|
| MIN | 44 | 31 | |
| MAX | 134 | 145 | |
| Placebo | | | |
| MEDEL | 73 | 63.4 | 14 |
| MEDIAN | 65.5 | 58.5 | |
| STDAV | 29.4 | 23.6 | |
| MIN | 34 | 26 | |
| MAX | 167 | 155 | |

Stroop Tests

The Stroop test (Victoria version) is a time-based test sensitive to frontal lobe dysfunction. It measures executive functioning and is validated and used internationally. Depression and anxiety could influence the results. Speeds of processing and conceptual abilities contribute to the performance. It also reflects the ability of concentration. The test consists of three cards each containing six rows of four items.

Stroop I is on the first card. In this subtest the subject must name as quickly as possible the color of 24 dots printed in blue, green, red and yellow. Each color is used six times and the four colors are arranged in pseudo-random order within the array, each color appears once in a row.

Stroop 2 is on the second card. In this subtest the dots are replaced by common words printed in lower-case letters. The subject is required to name the colors in which the stimuli are presented and to disregard their verbal content.

Stroop 3 is on the third card. In this subtest the colored stimuli are the color names "blue, green, red and yellow" printed in lower case letters so that the print color never corresponds to the color name.

Results:

Table 7 shows the results from the Stroop tests before and after treatment from patients treated with OSU6162 and patients treated with placebo. No significant differences were observed between the groups.

TABLE 7

Results from Stroop tests.

| | OSU6162 | Before | After | Difference | Placebo | Before | After | Difference |
|---|---|---|---|---|---|---|---|---|
| Stroop 1 | MEAN | 13.97 | 12.77 | 1.2 | MEAN | 14.57 | 12.97 | 1.6 |
| | MEDIAN | 14 | 12 | | MEDIAN | 13.5 | 12 | |
| | STDAV | 3.02 | 2.51 | | STDAV | 4.26 | 3.03 | |
| | MIN | 9 | 8 | | MIN | 9 | 9 | |
| | MAX | 22 | 20 | | MAX | 27 | 19 | |
| Stroop 2 | MEAN | 19.5 | 16.9 | 3.2 | MEAN | 19.7 | 16.6 | 3.2 |
| | MEDIAN | 19 | 16 | | MEDIAN | 26 | 21 | |
| | STDAV | 5.8 | 4.35 | | STDAV | 6.62 | 3.8 | |
| | MIN | 10 | 9 | | MIN | 13 | 12 | |
| | MAX | 39 | 29 | | MAX | 43 | 27 | |
| Stroop 3 | MEAN | 26.8 | 23.48 | 4.9 | MEAN | 27.63 | 22.4 | 5.6 |
| | MEDIAN | 24 | 23 | | MEDIAN | 26 | 21 | |
| | STDAV | 8.85 | 8.6 | | STDAV | 9.52 | 7.3 | |
| | MIN | 14 | 12 | | MIN | 13 | 15 | |
| | MAX | 51 | 62 | | MAX | 59 | 52 | |

In summary, no significant difference between the placebo treated and the OSU6162 treated groups was observed in the psychoneurological tests employed, indicating that treatment with OSU6162 does not affect the cognitive abilities of treated patients.

Itemized List of Embodiments

1. A dopamine stabilizing agent and an anti-depressive agent for use in the treatment of a disorder characterized by debilitating fatigue, wherein said dopamine stabilizing agent is selected from the group consisting of
   i) a compound of formula I

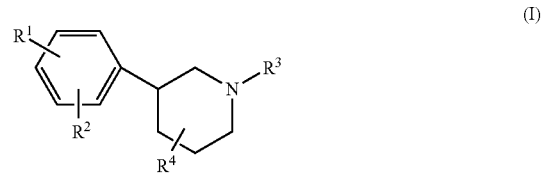

(I)

wherein:
   $R^1$ and $R^2$ are independently selected from the group consisting of H, provided that not more than one of $R^1$ and $R^2$ is H, $CONH_2$, OH, CN, $CH_2CN$, $OSO_2CH_3$, $OSO_2CF_3$, $SSO_2CF_3$, COR, $SO_xCH_3$, $SO_xCF_3$, $O(CH_2)_xCF_3$, where x is 0-2, $OSO_2N(R)_2$, CH=NOR, COCOOR, CO—COON(R)$_2$, $C_{3-8}$ cycloalkyl, $NRSO_2CF_3$, phenyl at position 2, 3 or 4, thienyl, furyl, pyrrolyl, oxazolyl, thiazolyl, N-pyrrolinyl, triazolyl and tetrazolyl of pyridinyl;
   $R^3$ is independently selected from the group consisting of H, $CF_3$, $CH_2CF_3$, $C_1$-$C_8$ alkyl, $C_3$-$C_8$ cycloalkyl, $C_4$-$C_9$ cycloalkyl-methyl, $C_2$-$C_8$ alkenyl, $C_2$-$C_8$ alkynyl, 3,3,3-trifluoropropyl, 4,4,4-trifluorobutyl and $CH_2SCH_3$,
   $R^4$ and R are independently selected from the group consisting of H, $CF_3CH_2CF_3$, $C_1$-$C_8$ alkyl, $C_3$-$C_8$ cycloalkyl, $C_4$-$C_9$ cycloalkyl-methyl, $C_2$-$C_8$ alkenyl, $C_2$-$C_8$ alkynyl, 3,3,3-trifluoropropyl, 4,4,4-trifluorobutyl and —(CH$_2$)m-$R^5$ where m is 1-8;
   $R^5$ is independently selected from the group consisting of phenyl, phenyl substituted with CN, $CF_3$, $CH_2CF_3$, $C_1$-$C_8$ alkyl, $C_3$-$C_8$ cycloalkyl, $C_4$-$C_9$ cycloalkyl-methyl, $C_2$-$C_8$ alkenyl or $C_2$-$C_8$ alkynyl substituent, 2-thiophenyl, 3-thiophenyl, —NR$^6$CONR$^6$R$^7$ and —CONR$^6$R$^7$; and
   $R^6$ and $R^7$ are independently selected from the group consisting of H, $C_1$-$C_8$ alkyl, $C_3$-$C_8$ cycloalkyl, $C_4$-$C_9$ cycloalkyl-methyl, $C_2$-$C_8$ alkenyl and $C_2$-$C_8$ alkynyl;
   ii) a compound of formula II

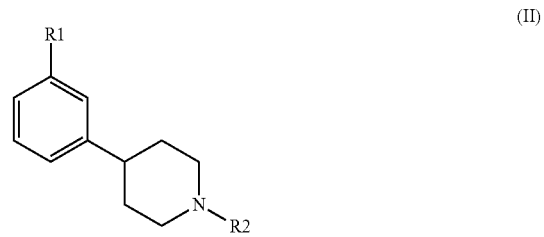

(II)

wherein:
R₁ is independently selected from the group consisting of OSO₂CF₃, OSO₂CH₃, SOR₃, SO₂R³, COCH₃ and COCH₂CH₃, wherein R₃ is as defined below;
R₂ is independently selected from the group consisting of C₂-C₄ branched or unbranched alkyls, terminal allyl, CH₂CH₂OCH₃, CH₂CH₂CH₂F, CH₂CF₃, 3,3, 3-trifluoropropyl and 4,4,4-trifluorobutyl, R₃ is independently selected from the group consisting of C₁-C₃ alkyls, CF₃, and N(CH₃)₂;
and
iii) a compound of formula III

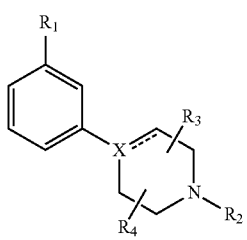

(III)

wherein:
X is independently selected from the group consisting of N, CH and C, provided that X may only be C when the compound comprises a double bond at the dotted line;
R₁ independently is selected from the group consisting of OSO₂CF₃, OSO₂CH₃, SOR₅, SO₂R⁵, COR₅, CN, NO₂, CONHR₅, CF₃, 3-thiophene, 2-thiophene, 3-furane, 2-furane, F, Cl, Br, and I, wherein R₅ is as defined below;
R₂ is independently selected from the group consisting of C₁-C₄ alkyls, allyls, CH₂SCH₃, CH₂CH₂OCH₃, CH₂CH₂CH₂F, CH₂CF₃, 3,3,3-trifluoropropyl, 4,4, 4-trifluorobutyl and —(CH₂)—R₆, wherein R₆ is as defined below;
R₃ and R₄ are independently selected from the group consisting of H and C₁-C₄ alkyls, provided that both R₃ and R₄ cannot be H at the same time;
R₅ is independently selected from the group consisting of C₁-C₃ alkyls, CF₃ and N(R₂)₂, wherein R₂ is as defined above; and
R₆ is independently selected from the group consisting of C₃-C₆ cycloalkyls, 2-tetrahydrofurane and 3-tetrahydrofurane;
and pharmaceutically acceptable salts of any one of the compounds of formula I, II or III.

2. A dopamine stabilizing agent and an anti-depressive agent for use according to item 1, wherein in formula I R¹ is independently selected from the group consisting of CN, OSO₂CF₃ and SO₂CH₃, such as CN.

3. A dopamine stabilizing agent and an anti-depressive agent for use according to item 1 or 2, wherein in formula I R² is H.

4. A dopamine stabilizing agent and an anti-depressive agent for use according to any one of items 1-3, wherein in formula I R³ is C₁₋₈ alkyl.

5. A dopamine stabilizing agent and an anti-depressive agent for use according to any one of items 1-4, wherein in formula I R³ is n-propyl.

6. A dopamine stabilizing agent and an anti-depressive agent for use according to any one of items 1-5, wherein in formula I R⁴ is H.

7. A dopamine stabilizing agent and an anti-depressive agent for use according to any preceding item, wherein said dopamine stabilizing agent is (3S)-3-[3-(methylsulfonyl)phenyl]-1-propylpiperidine or a pharmaceutically acceptable salt thereof, such as (3S)-3-[3-(methylsulfonyl)phenyl]-1-propylpiperidine hydrochloride.

8. A dopamine stabilizing agent and an anti-depressive agent for use according to any one of items 1-7, wherein said anti-depressive agent is selected from the group consisting of selective serotonin reuptake inhibitors (SSRIs), serotonin-norepinephrine reuptake inhibitors (SNRIs), serotonin modulators and stimulators (SMSs), serotonin reuptake inhibitors (SARIs), norephinephrine reuptake inhibitors (NRIs), tricyclic antidepressants (TCAs), monoamine oxidase inhibitors (MAOIs), tetracyclic antidepressants (TeCAs), noradrenergic and specific serotonergic antidepressant (NaSSAs), buprenorphine, low-dose antipsychotics and St John's wort, such as a group consisting of selective serotonin reuptake inhibitors (SSRIs), serotonin-norepinephrine reuptake inhibitors (SNRIs), serotonin modulators and stimulators (SMSs), serotonin reuptake inhibitors (SARIs), norephinephrine reuptake inhibitors (NRIs), tricyclic antidepressants (TCAs), tetracyclic antidepressants (TeCAs), noradrenergic and specific serotonergic antidepressant (NaSSAs), buprenorphine, low-dose antipsychotics and St John's wort 9. A dopamine stabilizing agent and an anti-depressive agent for use according to item 8, wherein the anti-depressive agent is selected from the group consisting of selective serotonin reuptake inhibitors (SSRI), serotonin-norepinephrine reuptake inhibitors (SNRI) and tricyclic antidepressants (TCAs), such as the group consisting of selective serotonin reuptake inhibitors (SSRI) and serotonin-norepinephrine reuptake inhibitors (SNRI).

10. A dopamine stabilizing agent and an anti-depressive agent for use according to item 9, wherein said selective serotonin reuptake inhibitor (SSRI) or serotonin-norepinephrine reuptake inhibitor (SNRI) is selected from the group consisting of escitalopram, citalopram, sertraline, fluoxetine, paroxetine, duloxetine, amitriptyline, fluvoxamine, dapoxetine, indalpine, zemelidinem venlafaxine, desvenlafaxine, milnacipran, levomilnacipran and sibutramine or combinations thereof.

11. A dopamine stabilizing agent and an anti-depressive agent for use according to item 9, wherein said selective serotonin reuptake inhibitors (SSRI), serotonin-norepinephrine reuptake inhibitors (SNRI) or tricyclic antidepressant (TCAs) is selected from the group consisting of escitalopram, citalopram, sertraline, fluoxetine, paroxetine, duloxetine, amitriptyline and venlafaxine or combinations thereof.

12. A dopamine stabilizing agent and an anti-depressive agent for use according to any one of items 1-11, wherein said use involves concomitant or simultaneous administration of said dopamine stabilizing agent and said anti-depressive agent.

13. A dopamine stabilizing agent and an anti-depressive agent for use according to item 12, wherein said concomitant administration is within less than 72 hours, such as within less than 48 hours, such as within less than 24 hours, such as within less than 12 hours, such as within less than 6 hours, such as within less than 1 hour.

14. A dopamine stabilizing agent and an anti-depressive agent for use according to any preceding item, wherein at least one or both of said dopamine stabilizing agent and said anti-depressive agent is/are administered orally, subcutaneously, intramuscularly or intravenously, such as orally.
15. A dopamine stabilizing agent and an anti-depressive agent for use according to any preceding item, wherein said dopamine stabilizing agent is administered in a dose of approximately 0.1-45 mg, such as 0.1-5 mg or such as approximately 1-45 mg, such as approximately 1-30 mg, such as approximately 5-30 mg, such as approximately 10-30 mg, such as 15 mg or 30 mg.
16. A dopamine stabilizing agent and an anti-depressive agent for use according to any preceding item, wherein said dopamine stabilizing agent is administered once, twice or three times a day, such as once or twice a day.
17. A dopamine stabilizing agent and an anti-depressive agent for use according to any preceding item, wherein, upon administration, the therapeutically effective blood plasma concentration of said dopamine stabilizing agent is approximately 0.1-0.7 µM, such as approximately 0.3-0.7 µM.
18. A dopamine stabilizing agent and an anti-depressive agent for use according to any preceding item, wherein said disorder is selected from the group consisting of myalgic encephalomyelitis/chronic fatigue syndrome, fibromyalgia, mental fatigue, post stroke fatigue, Huntington's disease, Parkinson's disease, multiple sclerosis, narcolepsy, post cancer fatigue, fatigue associated with cancer with or without cytostatic treatment, depression and combinations thereof.
19. A dopamine stabilizing agent and an anti-depressive agent for use according to any one of items 1-18, wherein said disorder is a fatigue disorder characterized by at least one of the conditions selected from fibromyalgia, mental fatigue, myalgic encephalomyelitis/chronic fatigue syndrome and depression.
20. A dopamine stabilizing agent and an anti-depressive agent for use according to any one of items 1-18, wherein said disorder is a pain disorder characterized by at least one of the conditions selected from fibromyalgia, mental fatigue, myalgic encephalomyelitis/chronic fatigue syndrome and depression.
21. A dopamine stabilizing agent and an anti-depressive agent for use according to item 18, wherein said disorder is selected from the group consisting of myalgic encephalomyelitis/chronic fatigue syndrome, mental fatigue, fibromyalgia, depression and combinations thereof.
22. A dopamine stabilizing agent and an anti-depressive agent for use according to item 21, wherein said disorder is myalgic encephalomyelitis/chronic fatigue syndrome.
23. A dopamine stabilizing agent and an anti-depressive agent for use according to item 21, wherein said disorder is mental fatigue.
24. A dopamine stabilizing agent and an anti-depressive agent for use according to item 21, wherein said disorder is depression
25. A dopamine stabilizing agent and an anti-depressive agent for use according to item 21, wherein said disorder is fibromyalgia.
26. A dopamine stabilizing agent and an anti-depressive agent for use according to item 21, wherein said disorder is a combination of selected from the group of a combination of myalgic encephalomyelitis/chronic fatigue syndrome and fibromyalgia; a combination of myalgic encephalomyelitis/chronic fatigue syndrome and mental fatigue; a combination of myalgic encephalomyelitis/chronic fatigue syndrome and depression; a combination of mental fatigue and depression; a combination of fibromyalgia and depression; and a combination of mental fatigue and fibromyalgia
27. A dopamine stabilizing agent and an anti-depressive agent for use according to item 21, wherein said disorder is a combination selected from a combination of myalgic encephalomyelitis/chronic fatigue syndrome, mental fatigue and fibromyalgia; a combination of myalgic encephalomyelitis/chronic fatigue syndrome, mental fatigue and depression; a combination of myalgic encephalomyelitis/chronic fatigue syndrome, depression and fibromyalgia; a combination of depression, mental fatigue and fibromyalgia.
28. Pharmaceutical composition comprising a dopamine stabilizing agent as defined in any one of items 1-7 and an anti-depressive agent.
29. Pharmaceutical composition according to item 28, wherein said anti-depressive agent is as defined in any one of items 8-11.
30. Pharmaceutical composition according to any one of items 28-29 wherein said composition is formulated for oral, subcutaneous, intramuscular or intravenous administration, such as for oral administration.
31. Pharmaceutical composition according to any one of items 28-30, comprising an amount of dopamine stabilizing agent of approximately 0.1-45 mg, such as 0.1-5 mg or such as approximately 1-45 mg, such as approximately 1-30 mg, such as approximately 5-30 mg, such as approximately 10-30 mg, such as 15 mg or 30 mg.
32. Pharmaceutical composition according to any one of items 26-31, wherein said composition is formulated as a pill, tablet, capsule, dragee, liquid, gel capsule, syrup, slurry or suspension, such as a pill.
33. Combination kit comprising a dopamine stabilizing agent as defined in any one of items 1-7 and an anti-depressive agent.
34. Combination kit according to item 31, wherein said anti-depressive agent is as defined in any one of items 8-11.
35. Combination kit according to item 33 or 34, wherein said dopamine stabilizing agent and said anti-depressive agent are formulated for concomitant or simultaneous administration.
36. Combination kit according to item 35, wherein said kit is formulated for concomitant administration within less than 72 hours, such as less than 48 hours, such as less than 24 hours, such as within less than 12 hours, such as within less than 6 hours, such as within less than 1 hour.
37. Combination kit according to item 35, wherein said kit is formulated for simultaneous administration.
38. Combination kit according to any one of items 33-37, wherein said kit is formulated for is oral, subcutaneous, intramuscular or intravenous administration, such as oral administration.
39. Combination kit according to any one of items 33-39, wherein said combination kit is formulated such that the dose of dopamine stabilizing agent of approximately 0.1-45 mg, such as 0.1-5 mg or such as approximately 1-45 mg, such as approximately 1-30 mg, such as approximately 5-30 mg, such as approximately 10-30 mg, such as 15 mg or 30 mg.

40. Dopamine stabilizing agent for use in the treatment of a disorder characterized by debilitating fatigue in a subject on treatment with at least one anti-depressive agent, wherein said dopamine stabilizing agent is as defined in any one of items 1-7.
41. Dopamine stabilizing agent for use according to item 40, wherein said disorder is as defined in any one of items 18-27.
42. Dopamine stabilizing agent for use according to any one of items 40-41, wherein said dopamine stabilizing agent is administered orally, subcutaneously, intramuscularly or intravenously, such as orally.
43. Dopamine stabilizing agent for use according to any one of items 38-40, wherein said dopamine stabilizing agent is administered as defined by any one of items 10-14.
44. Dopamine stabilizing agent for use according to any one of items 38-41, wherein said subject is on treatment with an anti-depressive agent as defined in any one of items 8-11.
45. Use of a dopamine stabilizing agent as defined in any one of items 1-7 and an anti-depressive agent, for the manufacture of a medicament for the treatment a disorder characterized by persistent and debilitating fatigue.
46. Use of a dopamine stabilizing agent according to item 45, wherein said anti-depressive agent as defined in any one of items 8-11, wherein said disorder is as defined in any one of items 18-27.
47. Use of a dopamine stabilizing agent as defined in any one of items 1-7, for the manufacture of a medicament for the treatment a disorder characterized by debilitating fatigue in a subject on treatment with at least one anti-depressive agent.
48. Method for treatment of a disorder characterized by debilitating fatigue, the method comprising administering to a subject in need thereof a therapeutically effective dose of a dopamine stabilizing agent, wherein said subject is on treatment with an anti-depressive agent, wherein the dopamine stabilizing agent is selected from the group consisting of
(i) a compound of formula I

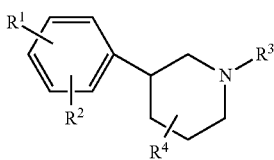

(I)

wherein:
R$^1$ and R$^2$ are independently selected from the group consisting of H, provided that not more than one of R$^1$ and R$^2$ is H, CONH$_2$, OH, CN, CH$_2$CN, OSO$_2$CH$_3$, OSO$_2$CF$_3$, SSO$_2$CF$_3$, COR, SO$_x$CH$_3$, SO$_x$CF$_3$, O(CH$_2$)$_x$CF$_3$, where x is 0-2, OSO$_2$N(R)$_2$, CH=NOR, COCOOR, CO—COON(R)$_2$, C$_{3-8}$ cycloalkyl, NRSO$_2$CF$_3$, phenyl at position 2, 3 or 4, thienyl, furyl, pyrrolyl, oxazolyl, thiazolyl, N-pyrrolinyl, triazolyl and tetrazolyl of pyridinyl;
R$^3$ is independently selected from the group consisting of H, CF$_3$, CH$_2$CF$_3$, C$_1$-C$_8$ alkyl, C$_3$-C$_8$ cycloalkyl, C$_4$-C$_9$ cycloalkyl-methyl, C$_2$-C$_8$ alkenyl, C$_2$-C$_8$ alkynyl, 3,3,3-trifluoropropyl, 4,4,4-trifluorobutyl and CH$_2$SCH$_3$, R$^4$ and R are independently selected from the group consisting of H, CF$_3$CH$_2$CF$_3$, C$_1$-C$_8$ alkyl, C$_3$-C$_8$ cycloalkyl, C$_4$-C$_9$ cycloalkyl-methyl, C$_2$-C$_8$ alkenyl, C$_2$-C$_8$ alkynyl, 3,3,3-trifluoropropyl, 4,4,4-trifluorobutyl and —(CH$_2$)m-R$^5$ where m is 1-8;
R$^5$ is independently selected from the group consisting of phenyl, phenyl substituted with CN, CF$_3$, CH$_2$CF$_3$, C$_1$-C$_8$ alkyl, C$_3$-C$_8$ cycloalkyl, C$_4$-C$_9$ cycloalkyl-methyl, C$_2$-C$_8$ alkenyl or C$_2$-C$_8$ alkynyl substituent, 2-thiophenyl, 3-thiophenyl, —NR$^6$CONR$^6$R$^7$ and —CONR$^6$R$^7$; and
R$^6$ and R$^7$ are independently selected from the group consisting of H, C$_1$-C$_8$ alkyl, C$_3$-C$_8$ cycloalkyl, C$_4$-C$_9$ cycloalkyl-methyl, C$_2$-C$_8$ alkenyl and C$_2$-C$_8$ alkynyl;
(ii) a compound of formula II

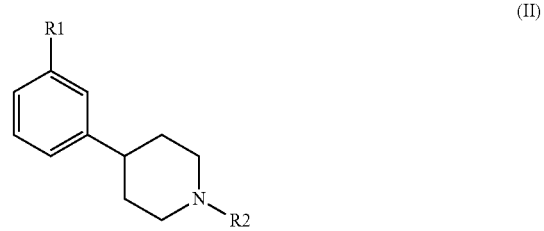

(II)

wherein:
R$_1$ is independently selected from the group consisting of OSO$_2$CF$_3$, OSO$_2$CH$_3$, SOR$_3$, SO$_2$R$^3$, COCH$_3$ and COCH$_2$CH$_3$, wherein R$_3$ is as defined below;
R$_2$ is independently selected from the group consisting of C$_2$-C$_4$ branched or unbranched alkyls, terminal allyl, CH$_2$CH$_2$OCH$_3$, CH$_2$CH$_2$CH$_2$F, CH$_2$CF$_3$, 3,3,3-trifluoropropyl and 4,4,4-trifluorobutyl, R$_3$ independently is selected from the group consisting of C$_1$-C$_3$ alkyls, CF$_3$, and N(CH$_3$)$_2$;
and
(iii) a compound of formula III

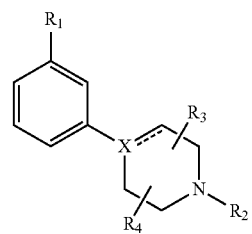

(III)

wherein:
X is independently selected from the group consisting of N, CH and C, provided that X may only be C when the compound comprises a double bond at the dotted line;
R$_1$ is independently selected from the group consisting of OSO$_2$CF$_3$, OSO$_2$CH$_3$, SOR$_5$, SO$_2$R$^5$, COR$_5$, CN, NO$_2$, CONHR$_5$, CF$_3$, 3-thiophene, 2-thiophene, 3-furane, 2-furane, F, Cl, Br, and I, wherein R$_5$ is as defined below;
R$_2$ is independently selected from the group consisting of C$_1$-C$_4$ alkyls, allyls, CH$_2$SCH$_3$, CH$_2$CH$_2$OCH$_3$, CH$_2$CH$_2$CH$_2$F, CH$_2$CF$_3$, 3,3,3-trifluoropropyl, 4,4,4-trifluorobutyl and —(CH$_2$)—R$_6$, wherein R$_6$ is defined below;

R₃ and R₄ are independently selected from the group consisting of H and $C_1$-$C_4$ alkyls, provided that both R₃ and R₄ cannot be H at the same time;

R₅ is independently selected from the group consisting of $C_1$-$C_3$ alkyls, $CF_3$ and $N(R_2)_2$, wherein R₂ is as defined above; and R₆ is selected from the group consisting of $C_3$-$C_6$ cycloalkyls, 2-tetrahydrofurane and 3-tetra-hydrofurane;

and pharmaceutically acceptable salts of any one of the compounds of formula I, II or III.

49. Method of treatment of a disorder characterized by debilitating fatigue according to item 48, wherein in formula I $R^1$ is independently selected from the group consisting of CN, $OSO_2CF_3$ and $SO_2CH_3$, such as CN.

50. Method of treatment of a disorder characterized by debilitating fatigue according to item 48 or 49, wherein in formula I $R^2$ is H 51. Method of treatment of a disorder characterized by debilitating fatigue according to any one of items 48-50, wherein in formula I $R^3$ is $C_{1-8}$ alkyl.

52. Method of treatment of a disorder characterized by debilitating fatigue according to any one of items 48-51, wherein in formula I $R^3$ is n-propyl.

53. Method of treatment of a disorder characterized by debilitating fatigue according to any one of items 48-52, wherein in formula I $R^4$ is H.

54. Method of treatment of a disorder characterized by debilitating fatigue according to any one of items 48-53, wherein said dopamine stabilizing agent is (3S)-3-[3-(methylsulfonyl)phenyl]-1-propylpiperidine or a pharmaceutically acceptable salt thereof, such as (3S)-3-[3-(methylsulfonyl)phenyl]-1-propylpiperidine hydrochloride.

55. Method of treatment of a disorder characterized by debilitating fatigue, the method comprising co-administration, to a subject in need thereof, of a therapeutically effective dose of a dopamine stabilizing agent and a therapeutically effective dose of an anti-depressive agent, wherein the dopamine stabilizing agent is defined as in any of one items 48-54.

56. Method of treatment according to any one of items 48-55, wherein said disorder is selected from the group consisting of myalgic encephalomyelitis/chronic fatigue syndrome, fibromyalgia, mental fatigue, post stroke fatigue, Huntington's disease, Parkinson's disease, multiple sclerosis, narcolepsy, post cancer fatigue, fatigue associated with cancer with or without cytostatic treatment, depression and combinations thereof.

57. Method of treatment according to any one of items 48-54, wherein said disorder is at least one fatigue disorder or pain disorder characterized by at least one of the conditions selected from fibromyalgia, mental fatigue, myalgic encephalomyelitis/chronic fatigue syndrome and depression.

58. Method of treatment according to item 55, wherein said disorder is at least one fatigue disorder or pain disorder characterized by at least one of the conditions selected from fibromyalgia, mental fatigue, depression and myalgic encephalomyelitis/chronic fatigue syndrome.

59. Method of treatment according to item 56, wherein the disorders is selected from the group consisting of myalgic encephalomyelitis/chronic fatigue syndrome; mental fatigue; fibromyalgia; depression; a combination of myalgic encephalomyelitis/chronic fatigue syndrome and fibromyalgia; a combination of myalgic encephalomyelitis/chronic fatigue syndrome and mental fatigue; a combination of myalgic encephalomyelitis/chronic fatigue syndrome and depression; a combination of mental fatigue and depression; a combination of fibromyalgia and depression; and a combination of mental fatigue and fibromyalgia; a combination of myalgic encephalomyelitis/chronic fatigue syndrome, mental fatigue and fibromyalgia; a combination of myalgic encephalomyelitis/chronic fatigue syndrome, mental fatigue and depression; a combination of myalgic encephalomyelitis/chronic fatigue syndrome, depression and fibromyalgia; a combination of depression, mental fatigue and fibromyalgia.

60. Method of treatment according to item 59, wherein the disorders is myalgic encephalomyelitis/chronic fatigue syndrome.

61. Method of treatment according to any one of items 48-60, wherein said anti-depressive agent is selected from the group consisting of the selective serotonin reuptake inhibitors (SSRIs), serotonin-norepinephrine reuptake inhibitors (SNRIs), serotonin modulators and stimulators (SMSs), serotonin reuptake inhibitors (SARIs), norephinephrine reuptake inhibitors (NRIs), tricyclic antidepressants (TCAs), monoamine oxidase inhibitors (MAOIs), tetracyclic antidepressants (TeCAs), noradrenergic and specific serotonergic antidepressant (NaSSAs), buprenorphine, low-dose antipsychotics and St John's wort, such as the group consisting of selective serotonin reuptake inhibitors (SSRI) and serotonin-norepinephrine reuptake inhibitors (SNRI).

62. Method of treatment according to item 61, wherein said selective serotonin reuptake inhibitor (SSRI), serotonin-norepinephrine reuptake inhibitor (SNRI) or tricyclic antidepressant (TCA) is selected from escitalopram, citalopram, sertraline, fluoxetine, paroxetine, duloxetine, amitriptyline, fluvoxamine, dapoxetine, indalpine, zemelidinem venlafaxine, desvenlafaxine, milnacipran, levomilnacipran and sibutramine or combinations thereof, such as the group consisting of escitalopram, citalopram, sertraline, fluoxetine, paroxetine, duloxetine, amitriptyline, venlafaxine or combinations thereof.

63. Method of treatment according to any one of items 46-55, wherein the co-administration is concomitant or simultaneous.

64. Method of treatment according to item 63, wherein said co-administration is concomitant administration within less than 72 hours, such as less than 48 hours, such as less than 24 hours, such as within less than 12 hours, such as within less than 6 hours, such as within less than 1 hour.

65. Method of treatment according to item 63, wherein said co-administration is simultaneous.

66. Method of treatment according to any one of items 48-65, wherein said dopamine stabilizing agent is administered orally, subcutaneously, intramuscularly or intravenously, such as orally.

67. Method of treatment according to any one of items 55-66, wherein said anti-depressive agent is administered orally, subcutaneously, intramuscularly or intravenously, such as orally.

68. Method of treatment according to item 48-67, wherein said dopamine stabilizing agent is administered in a dose of approximately 0.1-45 mg, such as 0.1-5 mg or such as approximately 1-45 mg, such as approximately 1-30 mg, such as approximately 5-30 mg, such as approximately 10-30 mg, such as 15 mg or 30 mg.

69. Method of treatment according to any one of items 48-68, wherein said dopamine stabilizing agent is administered once, twice or three times a day, such as once or twice a day.

70. Method of treatment according to any one of items 48-69, wherein, upon administration, the therapeutically effective blood plasma concentration of said dopamine stabilizing agent is approximately 0.1-0.7 µM, such as approximately 0.3-0.7 µM.

The invention claimed is:

1. A method of treating a subject for one or more symptoms of a disorder
    characterized by debilitating fatigue, comprising:
        administering therapeutic amounts of a dopamine stabilizing agent and an anti-depressive agent to the subject, wherein the dopamine stabilizing agent is 3-[3-(methylsulfonyl)phenyl]-1-propylpiperidine or a pharmaceutically acceptable salt thereof;
    wherein said anti-depressive agent is selected from the group consisting of escitalopram, citalopram, venlafaxine, sertraline, fluoxetine, paroxetine, duloxetine, amitriptyline, fluvoxamine, clomipramine, milnacipran, vortioxetine and vilazodone;
        wherein said disorder is selected from the group consisting of myalgic encephalomyelitis/chronic fatigue syndrome, fibromyalgia, mental fatigue, post stroke fatigue, Huntington's disease, Parkinson's disease, multiple sclerosis, narcolepsy, post cancer fatigue, fatigue associated with cancer with or without cytostatic treatment, depression, and combinations thereof; and
        wherein said one or more symptoms are selected from the group consisting of persistent and/or recurrent debilitating fatigue, diffuse musculoskeletal pain, sleep disturbances, neuropsychiatric symptoms, hopelessness, irritability and sadness.

2. The method of claim 1, wherein said dopamine stabilizing agent is (3S)-3-[3-(methylsulfonyl)phenyl]-1-propylpiperidine or a pharmaceutically acceptable salt thereof.

3. The method of claim 1, wherein said method involves concomitant or simultaneous administration of said dopamine stabilizing agent and said anti-depressive agent.

4. The method of claim 1, wherein said disorder is selected from the group consisting of fibromyalgia, mental fatigue, myalgic encephalomyelitis/chronic fatigue syndrome, Huntington's disease and depression.

5. The method of claim 1, wherein said dopamine stabilizing agent is administered in a dose of approximately 0.1-45 mg.

6. The method of claim 1, wherein said dopamine stabilizing agent is administered once, twice or three times a day.

7. The method of claim 1, wherein, upon administration, the therapeutically effective blood plasma concentration of said dopamine stabilizing agent is approximately 0.1-0.7 µM.

8. The method of claim 1, wherein the dopamine stabilizing agent is (3S)-3-[3-(methylsulfonyl)phenyl]-1-propylpiperidine hydrochloride.

9. The method of claim 1, wherein the said dopamine stabilizing agent is administered in a dose of approximately 0.1-5 mg, approximately 1-45 mg, approximately 1-30 mg, approximately 5-30 mg, or approximately 10-30 mg.

10. The method of claim 9, wherein the said dopamine stabilizing agent is administered in a dose of 15 mg or 30 mg.

11. The method of claim 7, wherein, upon administration, the therapeutically effective blood plasma concentration of said dopamine stabilizing agent is approximately 0.3-0.7 µM.

12. The method of claim 1, wherein administering comprises administering a pharmaceutical composition to the subject, wherein the pharmaceutical composition comprises both the dopamine stabilizing agent and the anti-depressive agent.

13. The method of claim 1, wherein said dopamine stabilizing agent and said anti-depressive agent are components of a kit.

* * * * *